(12) United States Patent
Hoitink et al.

(10) Patent No.: US 11,744,480 B2
(45) Date of Patent: Sep. 5, 2023

(54) CATHETER DEFLECTION SYSTEM WITH DEFLECTION LOAD LIMITER

(71) Applicant: Biosense Webster (Israel) Ltd., Yokneam (IL)

(72) Inventors: Ryan Hoitink, Glendale, CA (US); Ricardo Padilla, Jr., Eastvale, CA (US); Frank H. Truong, El Monte, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 73 days.

(21) Appl. No.: 15/930,795

(22) Filed: May 13, 2020

(65) Prior Publication Data

US 2020/0405182 A1 Dec. 31, 2020

Related U.S. Application Data

(60) Provisional application No. 62/866,109, filed on Jun. 25, 2019.

(51) Int. Cl.
*A61B 5/06* (2006.01)
*A61B 5/00* (2006.01)
(Continued)

(52) U.S. Cl.
CPC ............ *A61B 5/065* (2013.01); *A61B 5/6852* (2013.01); *A61B 18/1492* (2013.01); *A61B 34/20* (2016.02); *A61B 2017/00199* (2013.01); *A61B 2017/00327* (2013.01); *A61B 2018/00077* (2013.01); *A61B 2018/00351* (2013.01); *A61B 2018/00577* (2013.01); *A61B 2218/002* (2013.01)

(58) Field of Classification Search
None
See application file for complete search history.

(56) References Cited

U.S. PATENT DOCUMENTS

| 5,114,403 A | 5/1992 | Clarke et al. |
| 5,549,542 A | 8/1996 | Kovalcheck |

(Continued)

OTHER PUBLICATIONS

Extended European Search Report dated Oct. 29, 2020, for Application No. 20181883.8, 7 pages.

(Continued)

*Primary Examiner* — Shahdeep Mohammed
(74) *Attorney, Agent, or Firm* — Lewis Roca Rothgerber Christie LLP

(57) ABSTRACT

An apparatus includes a handle, a catheter, extending distally from the handle, an end effector extending distally from the catheter, a deflection assembly, and a load limiting assembly. The deflection assembly is configured to deflect the end effector away from a longitudinal axis of the catheter. The deflection assembly includes an input member and a translating assembly. The input member is configured to drive the translating assembly to deflect the end effector away from the longitudinal axis. The load limiting assembly is configured to decouple the input member from the translating assembly at a predetermined load such that the input member is inhibited from driving the translating assembly when the input member is decoupled by the load limiting assembly.

20 Claims, 26 Drawing Sheets

(51) Int. Cl.
*A61B 18/14* (2006.01)
*A61B 17/00* (2006.01)
*A61B 18/00* (2006.01)
*A61B 34/20* (2016.01)

(56) References Cited

U.S. PATENT DOCUMENTS

| | | | |
|---|---|---|---|
| 5,738,096 | A | 4/1998 | Ben-Haim |
| 6,325,972 | B1 | 12/2001 | Jacobs et al. |
| 6,365,102 | B1 | 4/2002 | Wu et al. |
| 6,447,719 | B1 | 9/2002 | Agamohamadi et al. |
| 6,852,277 | B2 | 2/2005 | Platt, Jr. |
| 6,852,279 | B2 | 2/2005 | Williams et al. |
| 6,939,519 | B2 | 9/2005 | Agamohamadi et al. |
| 8,231,569 | B2 | 7/2012 | Grasse et al. |
| 8,956,353 | B2 | 2/2015 | Govari et al. |
| 9,211,160 | B2 | 12/2015 | Pivotto et al. |
| 9,480,416 | B2 | 11/2016 | Govari et al. |
| 9,801,585 | B2 | 10/2017 | Shah et al. |
| 9,907,480 | B2 | 3/2018 | Basu et al. |
| 10,130,422 | B2 | 11/2018 | Ditter |
| 2004/0193015 | A1* | 9/2004 | Ikeda .................. A61B 1/0016 600/145 |
| 2012/0172703 | A1* | 7/2012 | Esguerra ............... A61B 5/062 600/409 |
| 2013/0030426 | A1 | 1/2013 | Gallardo et al. |
| 2014/0324015 | A1* | 10/2014 | Romoscanu ...... A61M 25/0147 604/95.05 |
| 2015/0105615 | A1* | 4/2015 | Kato ....................... A61B 1/05 600/109 |
| 2015/0320437 | A1* | 11/2015 | Worrell .............. A61B 18/1445 606/169 |
| 2017/0252474 | A1 | 9/2017 | Thompson et al. |
| 2017/0312022 | A1 | 11/2017 | Beeckler et al. |
| 2018/0056038 | A1 | 3/2018 | Aujla |
| 2018/0071017 | A1 | 3/2018 | Bar-tal et al. |
| 2019/0015646 | A1 | 1/2019 | Matlock et al. |

OTHER PUBLICATIONS

European Communication dated Aug. 31, 2022, for Application No. 20181883.8, 5 pages.

* cited by examiner

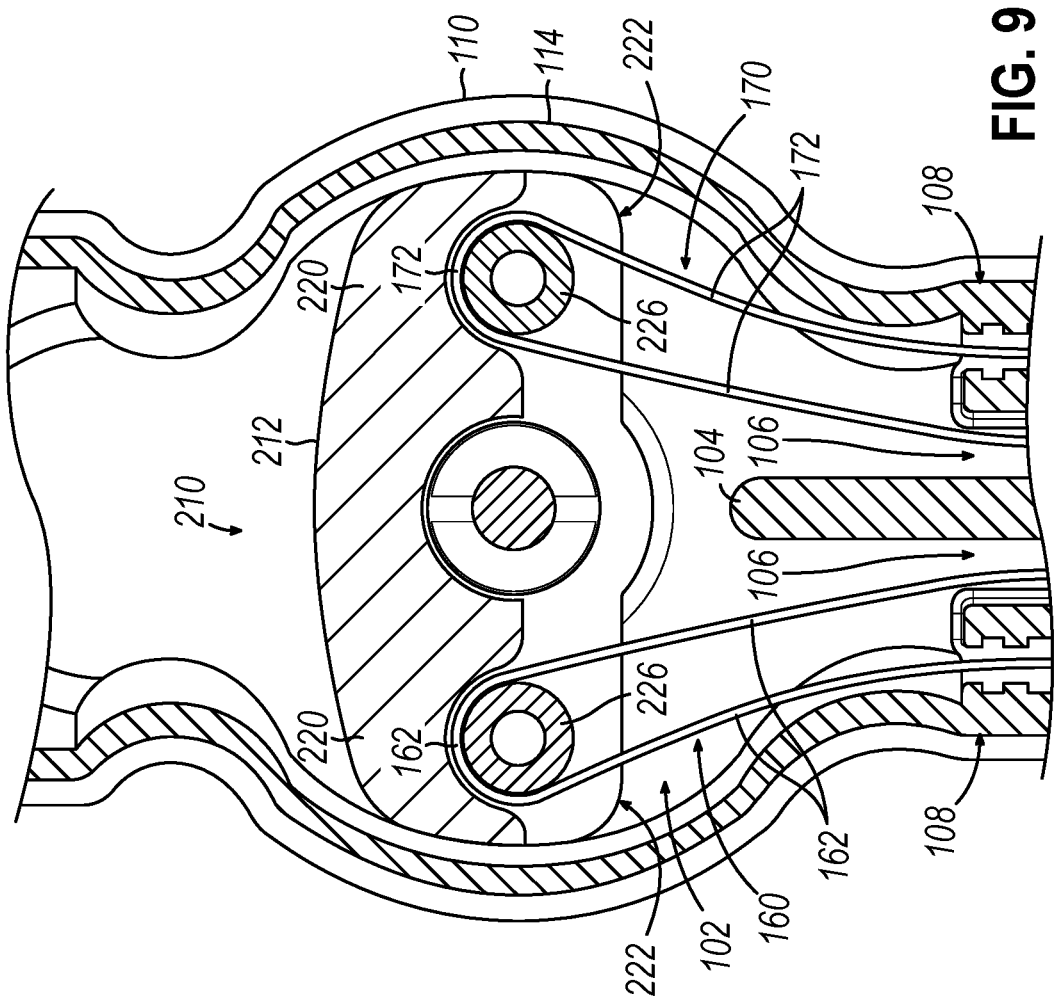

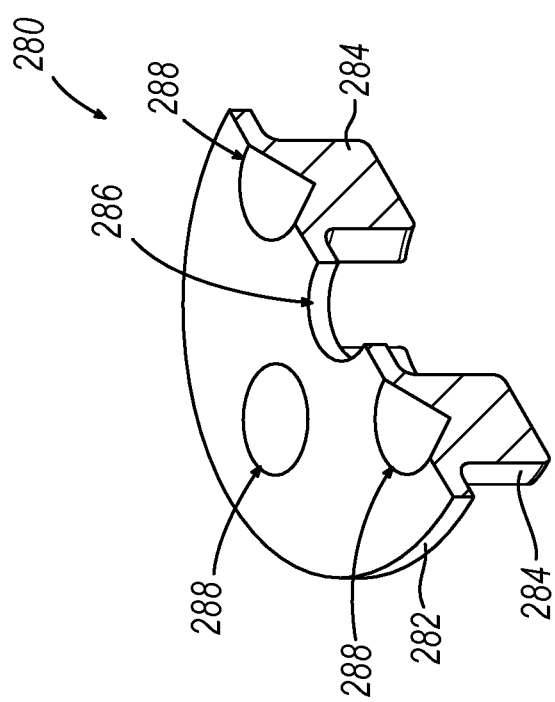

CATHETER DEFLECTION SYSTEM WITH DEFLECTION LOAD LIMITER

PRIORITY

This application claims priority to U.S. Provisional Patent App. No. 62/866,109, entitled "Catheter Deflection System with Deflection Load Limiter," filed Jun. 25, 2019, the disclosure of which is incorporated by reference herein in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The one or more electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad or other reference electrode that is in contact with the patient that is in contact with the patient. Irrigation may be used to draw heat from ablating components of an ablation catheter; and to prevent the formation of blood clots near the ablation site.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein, in its entirety; U.S. Pub. No. 2017/0312022, entitled "Irrigated Balloon Catheter with Flexible Circuit Electrode Assembly," published Nov. 2, 2017, the disclosure of which is incorporated by reference herein, in its entirety; U.S. Pub. No. 2018/0071017, entitled "Ablation Catheter with a Flexible Printed Circuit Board," published Mar. 15, 2018, the disclosure of which is incorporated by reference herein, in its entirety; U.S. Pub. No. 2018/0056038, entitled "Catheter with Bipole Electrode Spacer and Related Methods," published Mar. 1, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; U.S. Pat. No. 8,956,353, entitled "Electrode Irrigation Using Micro-Jets," issued Feb. 17, 2015, the disclosure of which is incorporated by reference herein, in its entirety; and U.S. Pat. No. 9,801,585, entitled "Electrocardiogram Noise Reduction," issued Oct. 31, 2017, the disclosure of which is incorporated by reference herein, in its entirety.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein, in its entirety. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; and U.S. Pub. No. 2018/0056038, entitled "Catheter with Bipole Electrode Spacer and Related Methods," published Mar. 1, 2018, the disclosure of which is incorporated by reference herein, in its entirety.

When using an ablation catheter, it may be desirable to ensure that the one or more electrodes of the ablation catheter are sufficiently contacting target tissue. For instance, it may be desirable to ensure that the one or more electrodes are contacting target tissue with enough force to effectively apply RF ablation energy to the tissue; while not applying a degree of force that might tend to undesirably damage the tissue. To that end, it may be desirable to include one or more force sensors or pressure sensors to detect sufficient contact between one or more electrodes of an ablation catheter and target tissue.

In addition to using force sensing or EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein, in its entirety; and various other references that are cited herein.

While several catheter systems and methods have been made and used, it is believed that no one prior to the inventors has made or used the invention described, illustrated and claimed herein.

BRIEF DESCRIPTION OF THE DRAWINGS

The drawings and detailed description that follow are intended to be merely illustrative and are not intended to limit the scope of the invention as contemplated by the inventors.

FIG. 9 depicts a cross-sectional view of the handle and the deflection drive assembly of FIG. 6, taken along line 9-9 of FIG. 8;

FIG. 20 depicts a cross-sectional perspective view of the cable drive coupling of FIG. 19, taken along line 20-20 of FIG. 19;

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g.

"about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Overview of Exemplary Ablation Catheter System

Figure 1:
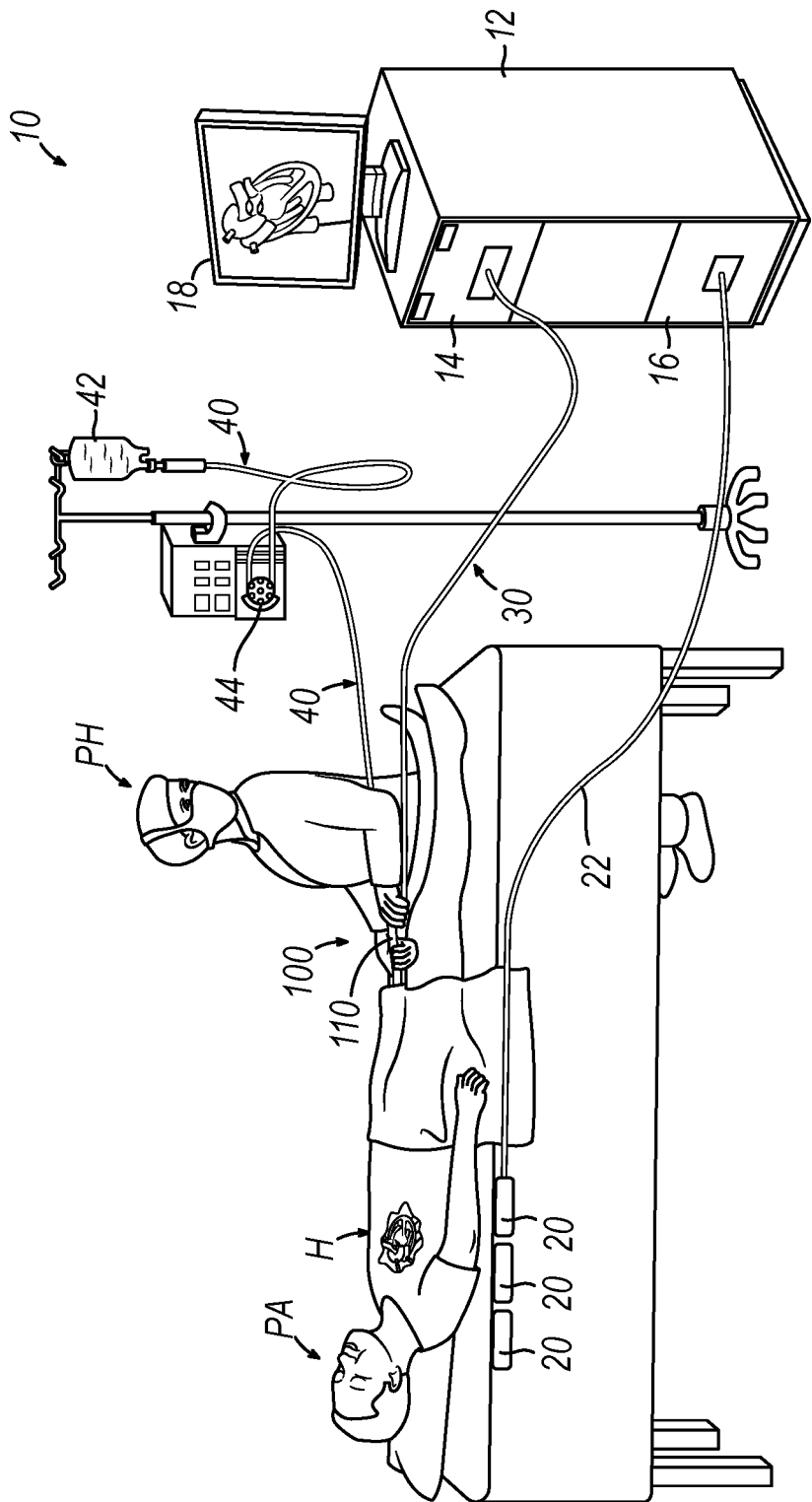
FIG. 1 depicts a schematic view of a medical procedure in which a catheter of a catheter assembly is inserted in a patient.
Figure 2:
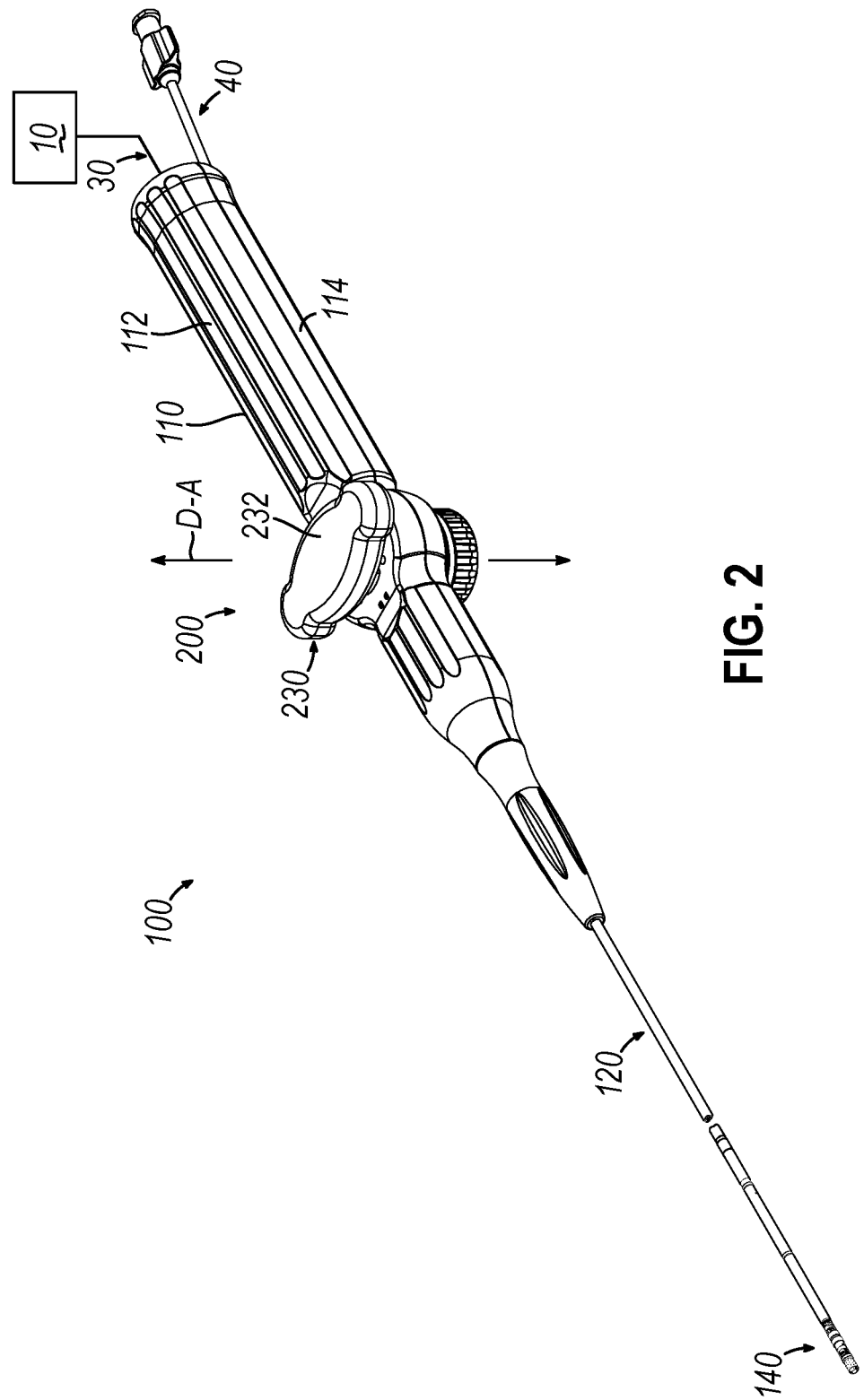
FIG. 2 depicts a perspective view of the catheter assembly of FIG. 1, with additional components shown in schematic form.

FIG. 1 shows an exemplary medical procedure and associated components of a cardiac ablation catheter system that may be used to provide cardiac ablation as referred to above. In particular, FIG. 1 shows a physician (PH) grasping a handle (110) of a catheter assembly (100), with an end effector (140) of a catheter (120) (shown in FIGS. 2-3 but not shown in FIG. 1) of catheter assembly (100) disposed in a patient (PA) to ablate tissue in or near the heart (H) of the patient (PA). As shown in FIG. 2, catheter assembly (100) includes handle (110), catheter (120) extending distally from handle (110), end effector (140) located at a distal end of catheter (120), and a deflection drive assembly (200) associated with handle (110).

As will be described in greater detail below, end effector (140) includes various components configured to deliver RF energy to targeted tissue sites, provide EP mapping functionality, track external forces imparted on end effector (140), track the location of end effector (140), and disperse irrigation fluid. As will also be described in greater detail below, deflection drive assembly (200) is configured to deflect end effector (140) and a distal portion of catheter (120) away from a central longitudinal axis (L-L) (FIGS. 3-5) defined by a proximal portion of catheter (120).

Figure 3:
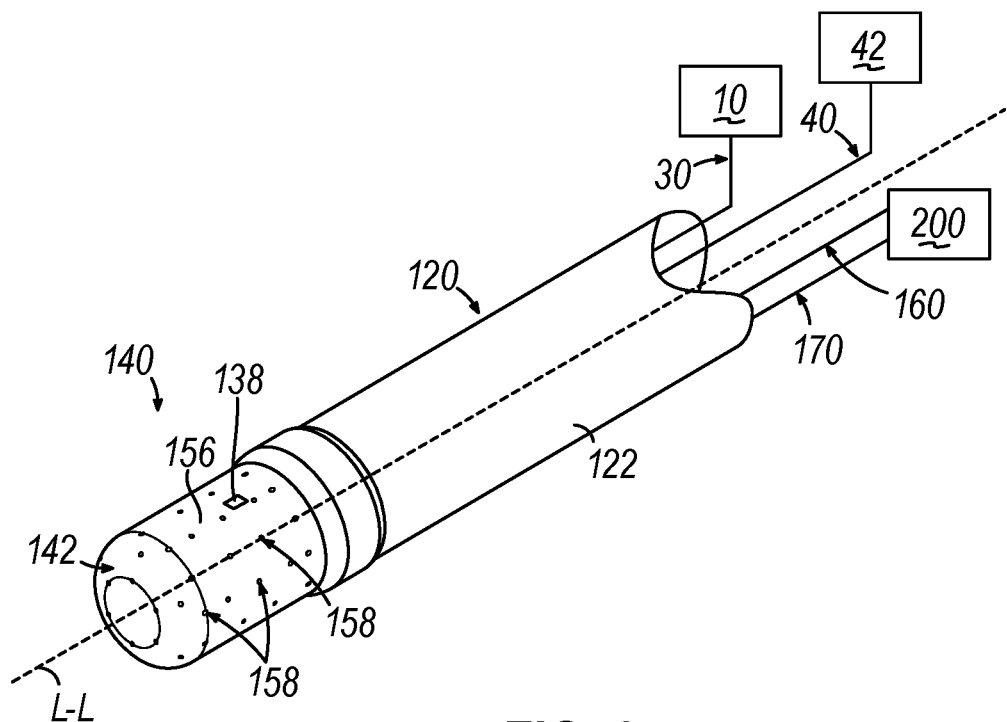
FIG. 3 depicts a perspective view of a distal portion of the catheter of FIG. 1, with additional components shown in schematic form.

As shown in FIG. 3, catheter (120) includes an elongate flexible sheath (122), with end effector (140) being disposed at a distal end of sheath (122). End effector (140) and various components that are contained in sheath (122) will be described in greater detail below. Catheter assembly (100) is coupled with a guidance and drive system (10) via a cable (30). Catheter assembly (100) is also coupled with a fluid source (42) via a fluid conduit (40). A set of field generators (20) are positioned underneath the patient (PA) and are coupled with guidance and drive system (10) via another cable (22). Field generators (20) are merely optional.

Guidance and drive system (10) of the present example include a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via microelectrodes (138) of end effector (140) as described in greater detail below. Console (12) includes a processor (not shown) that processes such EP mapping signals and thereby provides EP mapping as is known in the art.

First driver module (14) of the present example is further operable to provide RF power to a distal tip member (142) of end effector (140), as will be described in greater detail below, to thereby ablate tissue. Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

First driver module (14) is also operable to receive position indicative signals from a navigation sensor assembly (150) in end effector (140). In such versions, the processor of console (12) is also operable to process the position indicative signals from navigation sensor assembly (150) to thereby determine the position of end effector (140) within the patient (PA). As will be described in greater detail below, navigation sensor assembly (150) includes a pair of coils on respective panels (151) that are operable to generate signals that are indicative of the position and orientation of end effector (140) within the patient (PA). The coils are configured to generate electrical signals in response to the presence of an alternating electromagnetic field generated by field generators (20). Other components and techniques that may be used to generate real-time position data associated with end effector (140) may include wireless triangulation, acoustic tracking, optical tracking, inertial tracking, and the like. Alternatively, end effector (140) may lack a navigation sensor assembly (150).

Display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from navigation sensor assembly (150) of end effector (140). For instance, as end effector (140) of catheter (120) moves within the patient (PA), the corresponding position data from navigation sensor assembly (150) may cause the processor of console (12) to update the patient anatomy views in display (18) in real time to depict the regions of patient anatomy around end effector (140) as end effector (140) moves within the patient (PA). Moreover, the processor of console (12) may drive display (18) to show locations of aberrant conductive tissue sites, as detected via electrophysiological (EP) mapping with end effector (140) or as otherwise detected (e.g., using a dedicated EP mapping catheter, etc.). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (140) on the images of the patient's anatomy, such as by superimposing an illuminated dot, a crosshair, a graphical representation of end effector (140), or some other form of visual indication. Such a superimposed visual indication may also move within the images of the patient anatomy on display (18) in real time as the physician moves end effector (140) within the patient (PA), thereby providing real-time visual feedback to the operator about the position of end effector (140) within the patient (PA) as end effector (140) moves within the patient (PA). The images provided through display (18) may thus effectively provide a video tracking the position of end effector (140) within a patient (PA), without necessarily having any optical instrumentation (i.e., cameras) viewing end effector (140). In the same view, display (18) may simultaneously visually indicate the locations of aberrant conductive tissue sites detected through EP mapping. The physician (PH) may thus view display (18) to observe the real time positioning of end effector (140) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). As described in greater detail below, such irrigation fluid may be expelled through openings (158) of distal tip member (142) of end effector (140). Such irrigation may be provided in any suitable fashion as will be apparent to those skilled in the art in view of the teachings herein.

II. Exemplary End Effector of Catheter Assembly

Figure 4:
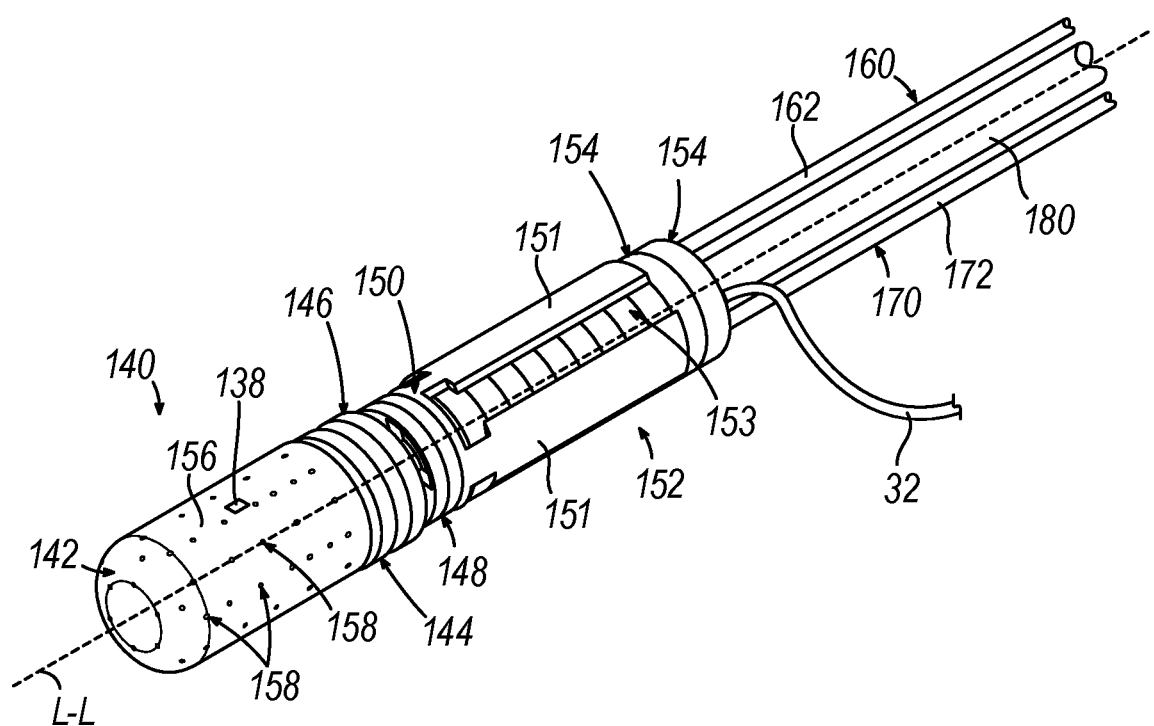
FIG. 4 depicts a perspective view of the distal portion of the catheter of FIG. 1, with an outer sheath omitted to reveal internal components.
Figure 5:
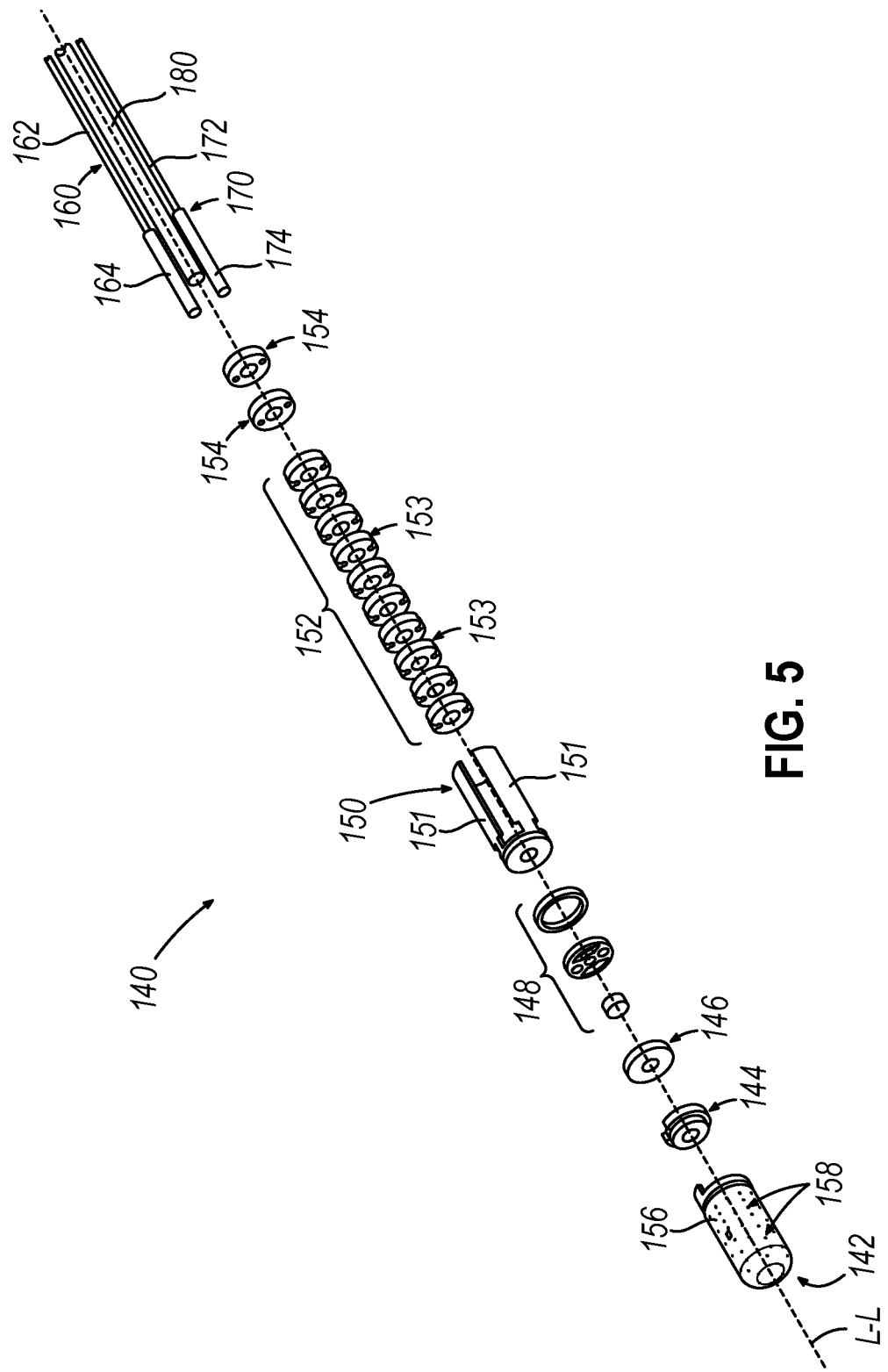
FIG. 5 depicts an exploded perspective view of the distal portion of the catheter of FIG. 1.
Figure 6:
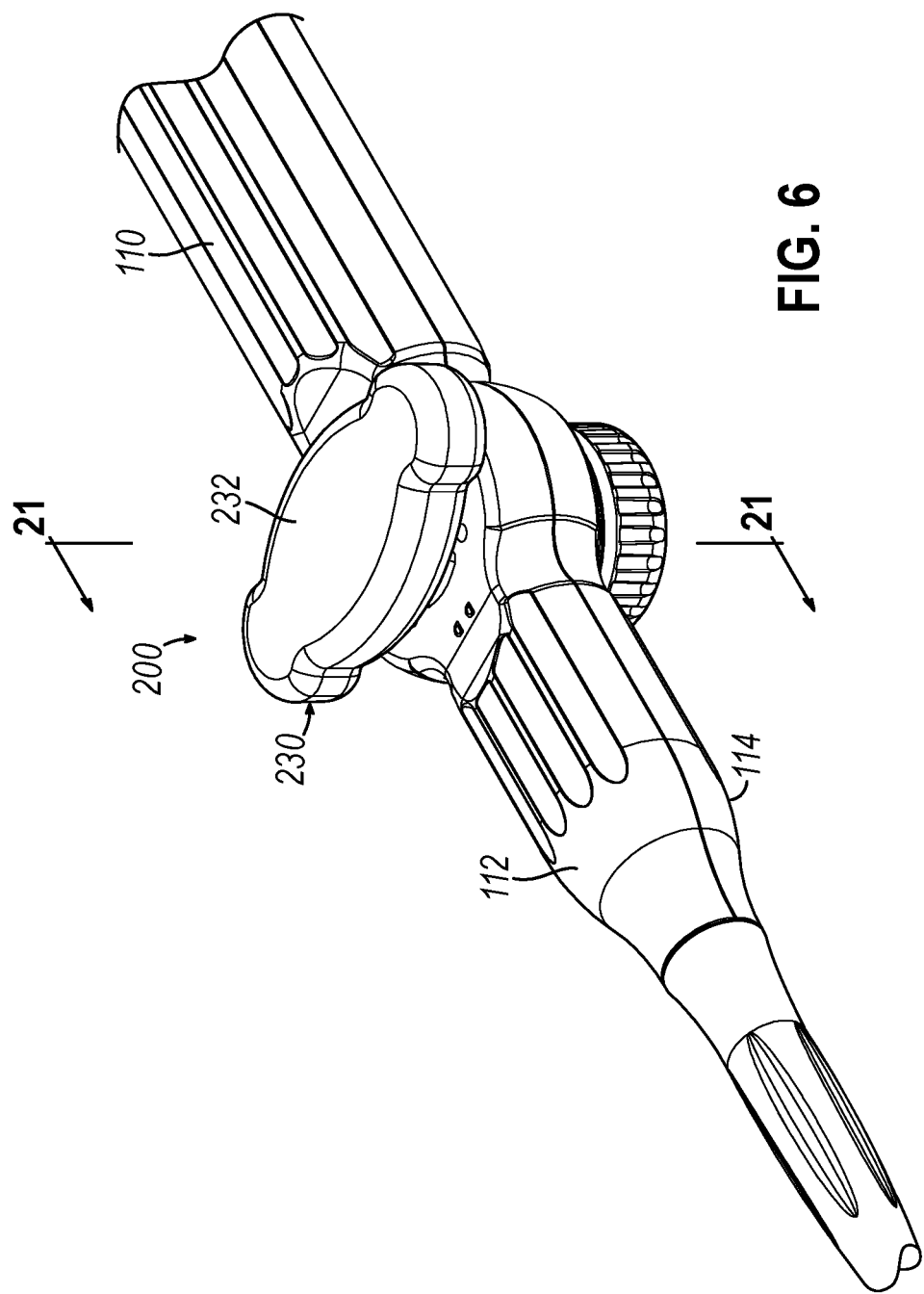
FIG. 6 depicts a perspective view of a handle and a deflection drive assembly of the catheter assembly of FIG. 1.

As mentioned above, end effector (140) includes various components configured to deliver RF energy to targeted tissue sites, provide EP mapping functionality, track external forces imparted on end effector (140), track the location of end effector (140) within the patient (PA), and disperse irrigation fluid. FIGS. 3-5 show exemplary components of end effector (140), and other components of the distal portion of catheter (120), in greater detail. End effector (140) includes a distal tip member (142), a distal tip base (144), a distal circuit disk (146), a strain gauge assembly (148), a navigation sensor assembly (150), a distal spacer stack (152), and a pair of proximal spacers (154). Distal tip member (142), distal tip base (144), distal circuit disk (146), strain gauge assembly (148), navigation sensor assembly (150), distal spacer stack (152), and proximal spacers (154) are coaxially aligned with each other and are stacked longitudinally so that these components (144-154) define a stacked circuit. A pair of push-pull cables (160, 170) and an irrigation tube (180) extend along the length of catheter (120) to reach end effector (140). Each of the foregoing components will be described in greater detail below. Flexible sheath (122) surrounds all of the foregoing components except for distal tip member (142).

As shown in FIGS. 4-5, distal tip member (142) of the present example includes a cylindraceous body (156) with a dome tip. Cylindraceous body (156) and the dome tip may be formed of an electrically conductive material, such as metal. A plurality of openings (158) are formed through cylindraceous body (156) and are in communication with the hollow interior of distal tip member (142). Openings (158) thus allow irrigation fluid to be communicated from the interior of distal tip member (142) out through cylindraceous body (156). Cylindraceous body (156) and the dome tip are also operable to apply RF electrical energy to tissue to thereby ablate the tissue. Such RF electrical energy may be communicated from first driver module (14) to the proximalmost spacer (154) via cable (30). Distal tip member (142) may also include one or more thermocouples that are configured to provide temperature sensing capabilities.

As shown in FIGS. 3-4, distal tip member (142) of the present example also includes one or more EP mapping microelectrodes (138) mounted to cylindraceous body (156). EP mapping microelectrodes (138) are configured to pick up electrical potentials from tissue that comes into contact with EP mapping microelectrodes (138). EP mapping microelectrodes (138) may thus be used to determine locations of aberrant electrical activity in tissue within a cardiovascular anatomical structure (e.g., pulmonary vein, etc.). Signals picked up by EP mapping microelectrodes (138) may be communicated through vias or other structures in the layers that are proximal to strain gauge assembly (148), eventually reaching first driver module (14) of console (12) via cable (30). First driver module (14) may process the EP mapping signals and provide the physician (PH) with corresponding feedback indicating the locations of aberrant electrical activity in accordance with the teachings of various references cited herein.

In versions where cylindraceous body (156) is formed of an electrically conductive material to provide RF electrical energy for tissue ablation, an electrically insulating material may be interposed between cylindraceous body (156) and EP mapping microelectrodes (138) to thereby electrically isolate EP mapping microelectrodes (138) from cylindraceous body (156). EP mapping microelectrodes (138) may be constructed and operable in accordance with the teachings of various patent references cited herein. While only one EP mapping microelectrode (138) is shown, distal tip member (142) may include two or more EP mapping microelectrodes (138). Alternatively, distal tip member (142) may lack EP mapping microelectrodes (138) altogether.

Distal tip base (144) defines a central aperture configured to provide a path for communication of irrigation fluid to the hollow interior of distal tip member (142). Distal tip base (144) forms an annular shoulder that the proximal edge of distal tip member (142) may abut. Distal tip member (142) also defines a lateral notch that is configured to receive a proximally extending tab of distal tip member (142). As shown in FIGS. 3-4, distal circuit disk (146) is positioned proximal to distal tip base (144). Distal circuit disk (146) includes circuitry that is operable to communicate RF electrical energy to distal tip member (142) via the proximally extending tab of distal tip member (142). In versions where one or more EP mapping electrodes (138) are included, distal circuit disk (146) may also include circuitry that is operable to communicate EP mapping signals from EP mapping electrodes (138).

In some versions, distal circuit disk (146) further includes one or more transmission coils. Such transmission coils may provide wireless communication of signals (e.g., EP mapping signals from microelectrodes (138)) to one or more complementary coils that are proximal to distal circuit disk (146). In addition, or in the alternative, such transmission coils may provide wireless communication of RF electrical energy from one or more complementary coils that are proximal to distal circuit disk (146) to distal tip member (142). In versions where coils are incorporated into distal circuit disk (146) and one or more other layers that are proximal to strain gauge assembly (148), such coils may thus enable wireless communication of electrical signals across strain gauge assembly (148) without requiring wires, vias, or other electrically conductive structures to pass longitudinally across strain gauge assembly (148).

In some versions, distal circuit disk (146) includes at least one transmission coil (TX) that is paired with receiving coil (RX) of navigation sensor assembly (150) to detect strain being applied to strain gauge assembly (148) so as to determine the contact force applied to distal tip (142). Some other versions of distal circuit disk (146) may simply omit a TX coil.

Strain gauge assembly (148) is positioned proximal to distal circuit disk (146) and is configured to sense external forces that impinge against distal tip member (142). When distal tip (142) encounters external forces (e.g., when distal tip (142) is pressed against tissue), those external forces are communicated from distal tip (142) to distal tip base (144), to distal circuit disk (146), and to strain gauge assembly (148) such that strain gauge may generate a suitable signal corresponding to the magnitude and direction of the external force. The signals from strain gauge assembly (148) may be communicated through vias or other structures in the layers that are proximal to strain gauge assembly (148), eventually reaching first driver module (14) of console (12) via cable (30). First driver module (14) may process the strain signals in accordance with any suitable fashion as would be apparent to one of ordinary skill in the art in view of the teachings herein. By way of example only, console (12) may provide audible feedback to alert the physician (PH) when strain gauge assembly (148) indicates that distal tip member (142)

is encountering forces over a predetermined threshold, to thereby prevent the physician (PH) from unwittingly damaging a cardiovascular anatomical structure with distal tip member (142).

Navigation sensor assembly (150) may generate signals indicating the position and orientation of end effector (140) in three-dimensional space with substantial precision. Navigation sensor assembly (150) includes a plurality of panels (151), each including an RX coil that is operable to generate position-indicative electrical signals in response to the alternating magnetic fields generated by field generators (20). Each RX coil may be formed by electrical traces to define an electrical coil or antenna to receive radiofrequency signals emitted by external transmitters TX coils (e.g., three TX coils provided by field generators (20) positioned external of the patient (PA) body and emitting discrete radiofrequencies) such that the location and orientation of each RX coil can be determined with respect to the TX coils provided by field generators (20). The signals from navigation sensor assembly (150) may be communicated through vias or other structures in the layers that are proximal to strain navigation sensor assembly (150), eventually reaching first driver module (14) of console (12) via cable (30).

A central annular body of navigation sensor assembly (150) defines a central aperture configured to provide a path for communication of irrigation fluid to the hollow interior of distal tip member (142). In versions where central annular body of navigation sensor assembly includes wireless communication coils, such wireless communication coils may be further coupled with vias or other structures in the layers that are proximal to strain navigation sensor assembly (150), thereby providing a path for electrical communication with first driver module (14) of console (12) via cable (30).

In the present example, each distal spacer (153) is generally shaped like a disk, with a pair of chordal cutouts angularly offset from each other by 90 degrees. These cutouts are sized and configured to accommodate a respective panel (151) of navigation sensor assembly (150), thereby allowing panels (151) to be radially interposed between distal spacer stack (152) and sheath (122). Each distal spacer (153) also includes a pair of cable notches that are angularly offset from each other by 180 degrees. These cable notches are configured to receive a respective distal end portion (174, 164) of push-pull cables (170, 172). Each distal spacer (153) further includes a central aperture configured to provide a path for communication of irrigation fluid to the hollow interior of distal tip member (142).

Each proximal spacer (154) is shaped like a disk, with three apertures formed therethrough. A central aperture is configured to provide a path for communication of irrigation fluid to the hollow interior of distal tip member (142). The side apertures are sized and configured to receive proximal portions (162, 172) of a respective push-pull cable (160, 170).

As noted above and as shown in FIGS. 1 and 3, cable (30) couples catheter assembly (100) with drive system (10). As shown in FIG. 4, wires (32) of cable (30) extend along the length of catheter (120) to reach the proximal-most proximal spacer (154). Wires (32) may thus be contained within sheath (122). Wires (32) may be physically and electrically coupled with the proximal-most proximal spacer (154) in any suitable fashion.

As also noted above, catheter assembly (100) is configured to enable irrigation fluid to be communicated from fluid source (42) to catheter (120) via fluid conduit (40), thereby providing expulsion of the irrigation fluid via openings (158) of distal tip member (142). In the present example, the fluid path for the irrigation fluid includes an irrigation tube (180), which is shown in FIGS. 4-5. The proximal end of irrigation tube (180) is coupled with fluid conduit (40) (e.g., at handle (110) of catheter assembly (100)). Irrigation tube (180) extends along the length of catheter (120) to reach end effector (140). In some versions, irrigation fluid may be communicated from the distal end of irrigation tube (180) through the central passageway formed by the aligned by the above-mentioned central apertures, ultimately reaching the interior of distal tip member (142) via aperture (218) of distal tip base (144).

III. Exemplary Handle and Deflection Drive of Catheter Assembly

As noted above, catheter assembly (100) includes a deflection drive assembly (200) configured to deflect end effector (140) away from the central longitudinal axis (L-L) defined by a proximal portion of catheter (120). Deflection drive assembly (200) of the present example includes push-pull cables (160, 170), a cable driver assembly (210), a rocker arm (230), and a load limiter assembly (250). As will be described in greater detail below, the physician (PA) may actuate rocker arm (230) relative to handle (110) such that cable driver assembly (210) actuates push-pull cables (160, 170) in a simultaneous, longitudinally-opposing motion to selectively deflect end effector (140) laterally away from a longitudinal axis (L-L), thereby enabling the physician (PH) to actively steer end effector (140) within the patient (PA).

Figure 7:
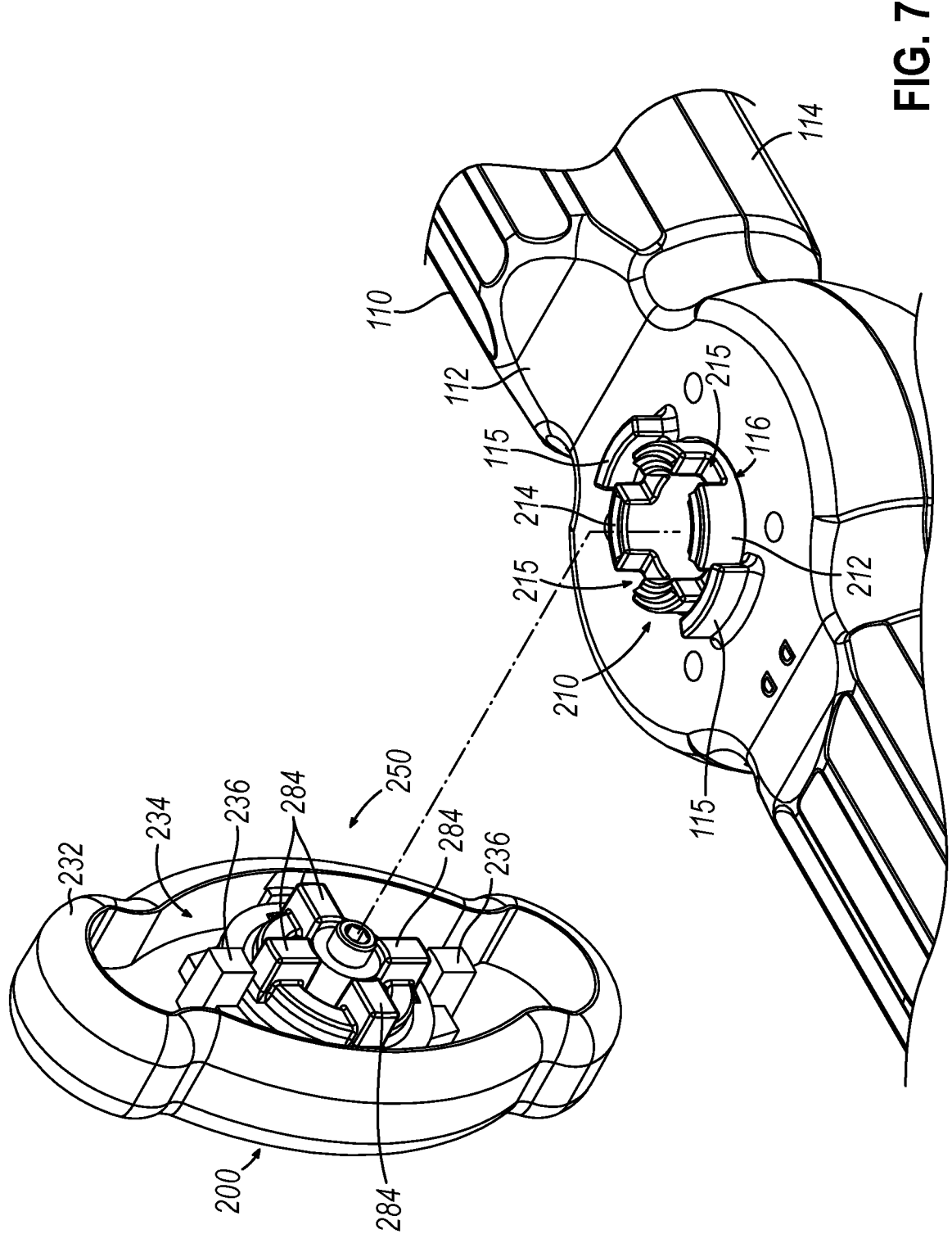
FIG. 7 depicts an exploded perspective view of the handle and the deflection drive assembly of FIG. 6.

Selected portions of deflection drive assembly (200) are operatively coupled to handle (110). Handle (110) includes a first casing portion (112) and a second casing portion (114) together defining an internal cavity (102). As beset seen in FIG. 7, first casing portion (112) defines a through hole (116) dimensioned to rotatably house a central body (212) of cable driver assembly (210). Rocker arm (230) may suitably couple with central body (212) in accordance with description herein. Additionally, first casing portion (112) includes a pair of stops (115) located on opposite sides of through hole (116). Stops (115) are configured to limit the rotation of rocker arm (230) relative to handle (110), to thereby limit the rotation of cable driver assembly (210) relative to handle (110).

Figure 8:
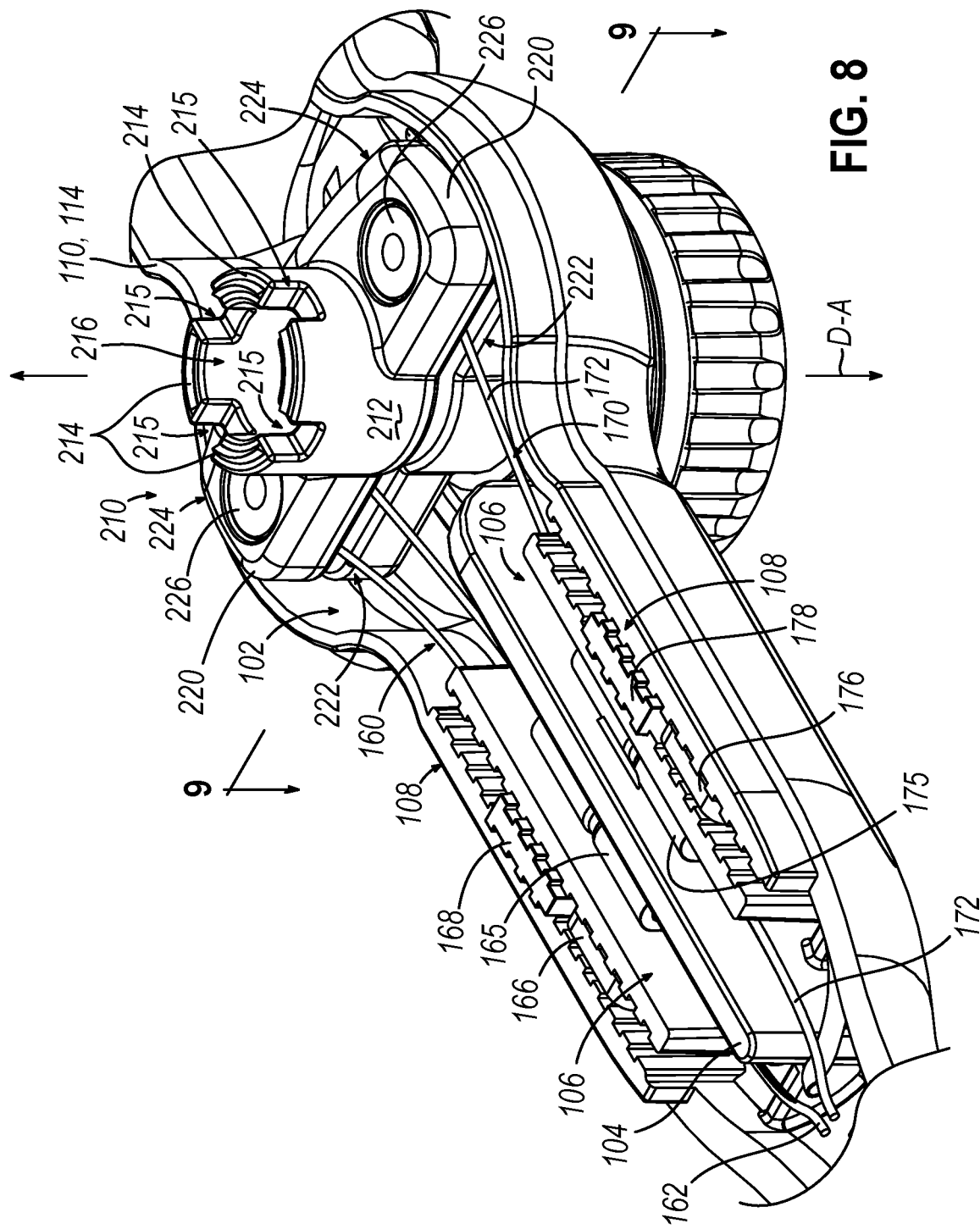
FIG. 8 depicts a perspective view of the handle and the deflection drive assembly of FIG. 6, with a portion of the handle omitted to reveal internal components.

As best seen in FIG. 8, an interior of second casing portion (114) includes a partition wall (104) and a pair of tension adjustment channels (108) located on opposite lateral sides of partition wall (104). Partition wall (104) and respective tension adjustment channels (108) together define a sliding channel (106). Each sliding channel (106) slidably houses a respective sliding body (165, 175). Sliding bodies (165, 175) are attached to respective push-pull cables (160, 170). Sliding bodies (165, 175) and sliding channels (106) may together assist in guiding the simultaneous opposing translation of portions of push-pull cables (160, 170) extending distally from sliding bodies (165, 175) in accordance with the description herein.

Tension adjustment channels (108) include a linear array laterally extending, rectangular projections. Tension adjustment channels (108) are configured to receive respective tension blocks (168, 178), which also each have a complementary linear array of laterally extending rectangular projections. The complementary rectangular projections of tensions blocks (168, 178) and tension adjustment channels (108) are configured to longitudinally fix tension blocks (168, 178) relative to second casing portion (114). In other words, tensions adjustment channels (108) are configured to receive tension blocks (168, 178) in a tongue-and-groove fashion to fix tension blocks (168, 178) relative to handle (110). Tensions blocks (168, 178) may be selectively inserted along various suitable locations within adjustment channels (108) in order to serve as a mechanical ground for push-pull cables (160, 170). Tension blocks (168, 178) may be inserted along various locations within adjustment channels (108) in order to adjust the tension within push-pull cables (160, 170) to thereby accommodate for length variations of push-pull cables (160, 170) due to various factors, such as manufacturing tolerance variations, deformation of push-pull cables (160, 170), etc.

Push-pull cables (160, 170) include respective intermediary portions (162, 172), distal portions (164, 174) (as best seen in FIG. 5), and proximal end blocks (166, 176) (as best seen in FIGS. 8 and 12A-12C. As best seen in FIGS. 8 and 12A-12C, proximal end blocks (166, 176) are housed within tension adjustment channels (108) just distal to tension blocks (168, 178). Tension blocks (168, 178) therefore prevent proximal end blocks (166, 176) from actuating proximally within adjustment channels (108), thereby serving as a mechanical ground for push-pull cables (160, 170). Proximal end blocks (166, 176) are fixed to respective intermediary portions (162, 172). Tension blocks (168, 178) define a through hole that intermediary portions (162, 172) extend through such that intermediary portions (162, 172) may extend from proximal end blocks (166, 176) through adjustment channels (108) in order to suitably couple with cable driver assembly (210). Alternatively, tension blocks (168, 178) and respective proximal end blocks (166, 176) may be formed of a single piece.

As best shown in FIG. 5, respective distal portions (164, 174) have a larger outer diameter than the outer diameter of respective intermediary portions (162, 172). Distal end portions (174, 164) are coupled with end effector (140) to prevent push-pull cables (160, 170) from being pulled proximally out of end effector (140). Suitable ways in which push-pull cables (160, 170) may be coupled with end effector (140) will be apparent to those skilled in the art in view of the teachings herein.

Figure 11A:
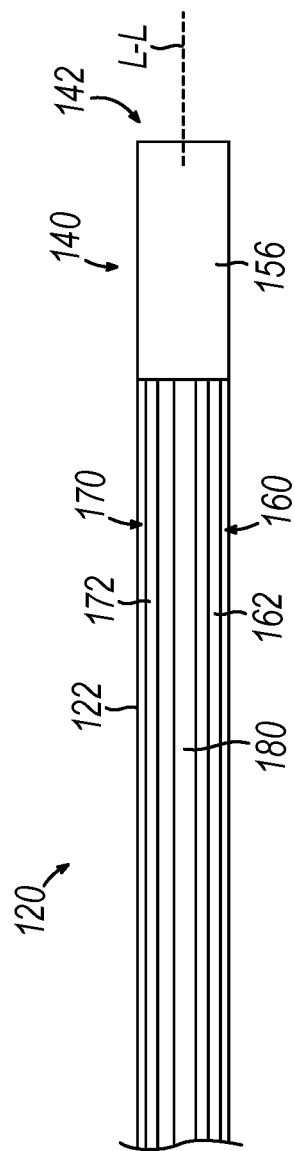
FIG. 11A depicts a top plan view of the distal portion of the catheter of FIG. 1, with a portion of the outer sheath omitted to reveal internal components, where the distal portion of the catheter is in a non-deflected position associated with the first rotational position of the elongated body of FIG. 10A.
Figure 11B:
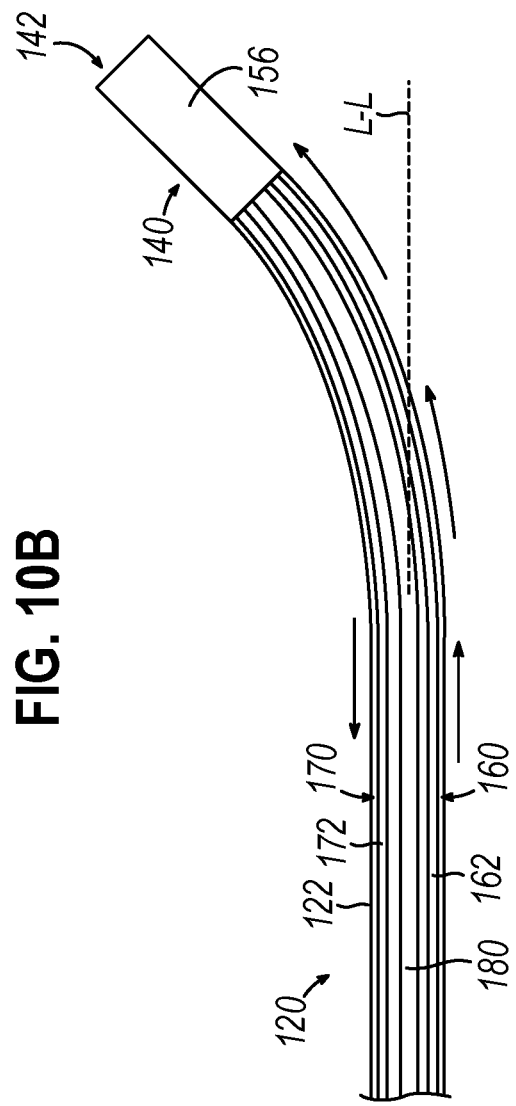
FIG. 11B depicts a top plan view of the distal portion of the catheter of FIG. 1, with a portion of the outer sheath omitted to reveal internal components, where the distal portion of the catheter is in a first deflected position associated with the second rotational position of the elongated body of FIG. 10B.
Figure 11C:
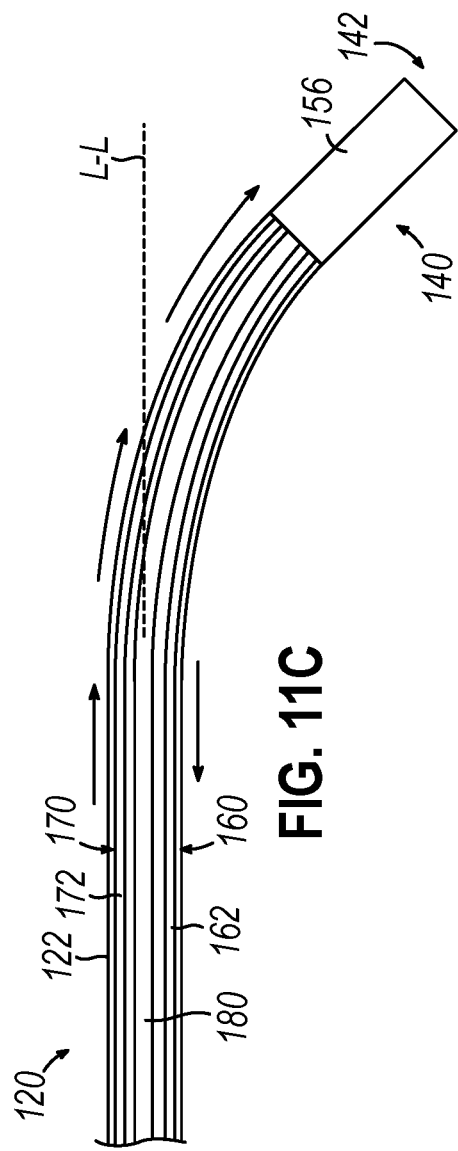
FIG. 11C depicts a top plan view of the distal portion of the catheter of FIG. 1, with a portion of the outer sheath omitted to reveal internal components, where the distal portion of the catheter is in a second deflected position associated with the third rotational position of the elongated body of FIG. 10C.
Figure 12A:
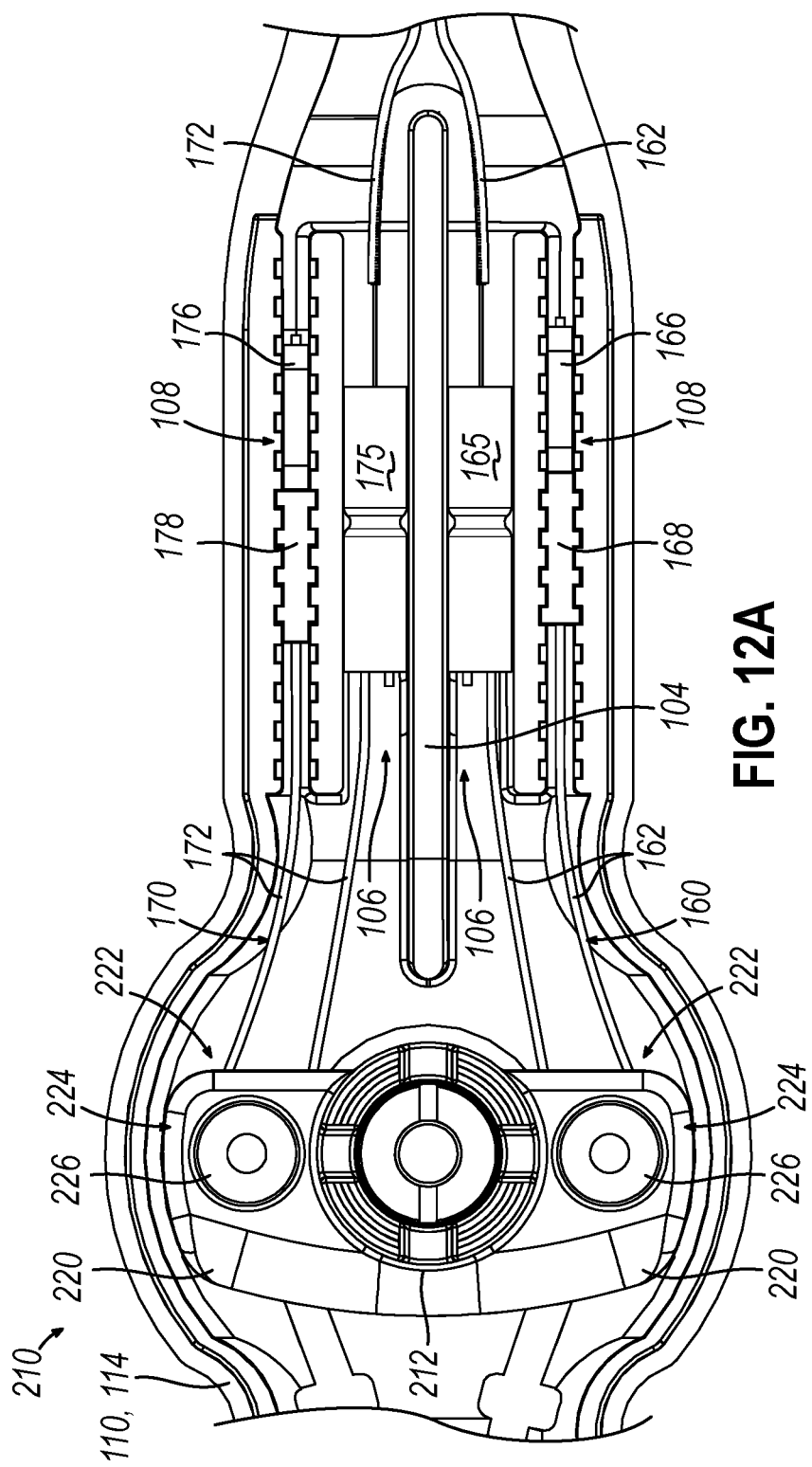
FIG. 12A depicts a top plan view of the handle and the deflection drive assembly of FIG. 6, with a portion of the handle omitted to reveal internal components, where the elongated body of FIG. 10A is in a first rotational position relative to the handle.
Figure 12B:
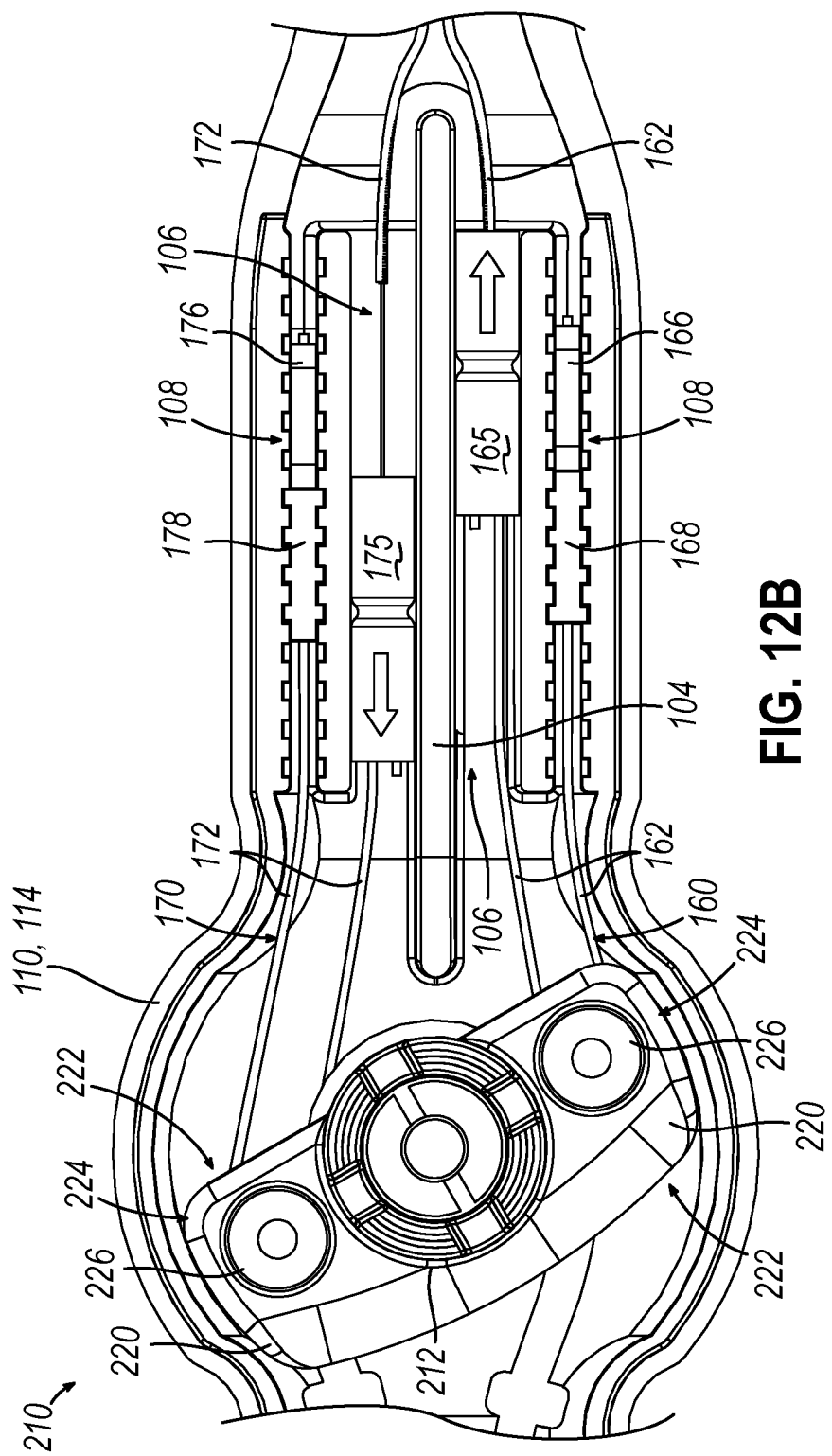
FIG. 12B depicts a top plan view of the handle and the deflection drive assembly of FIG. 6, with a portion of the handle omitted to reveal internal components, where the elongated body of FIG. 10A is in a second rotational position relative to the handle.
Figure 12C:
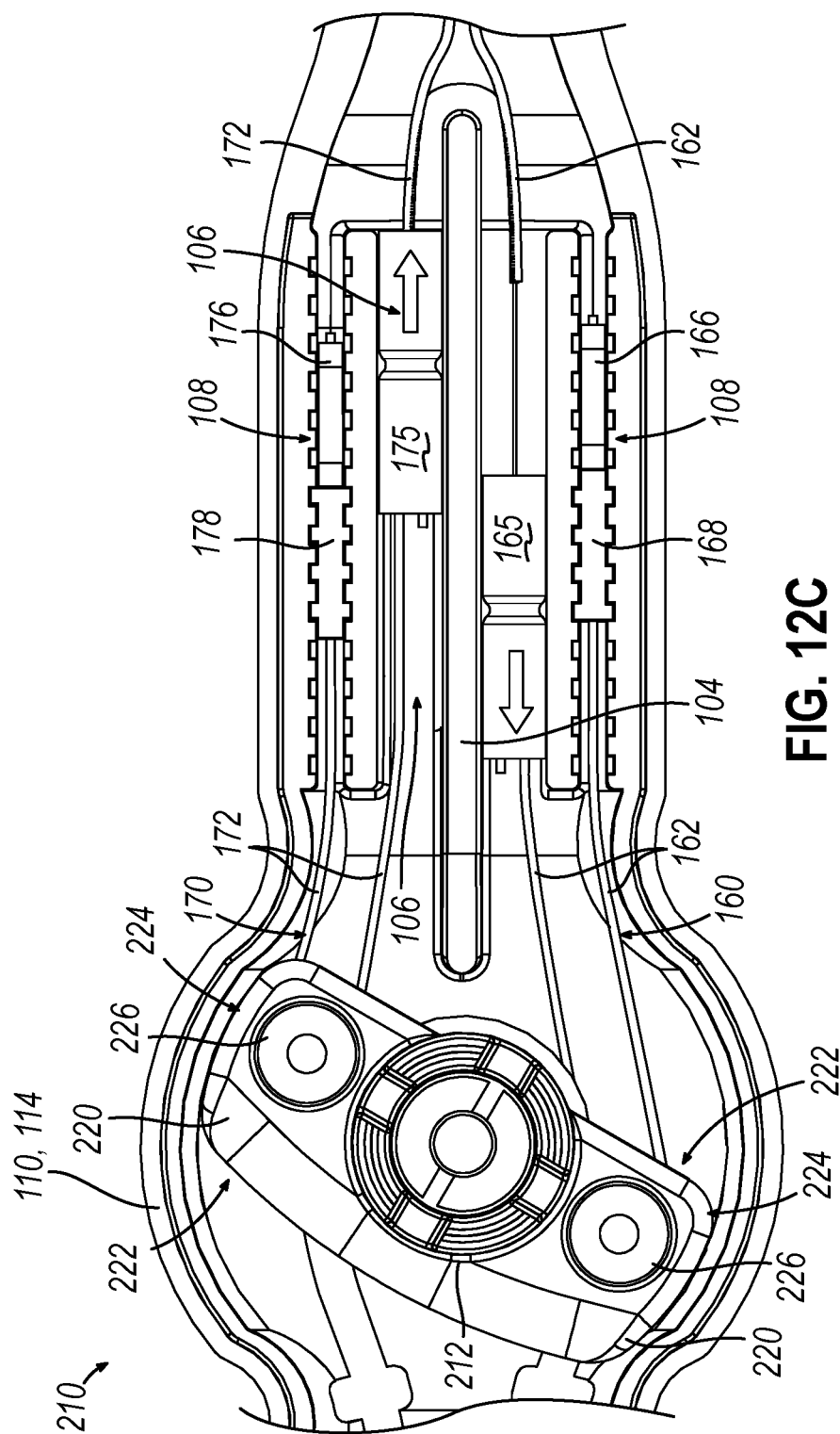
FIG. 12C depicts a top plan view of the handle and the deflection drive assembly of FIG. 6, with a portion of the handle omitted to reveal internal components, where the elongated body of FIG. 10A is in a third rotational position relative to the handle.

Intermediary portions (162, 172) extend proximally from distal portions (164, 174), through elongate flexible sheath (122) of catheter (120) (as best shown in FIGS. 11A-11C), into cable driver assembly (210) (as best shown in FIG. 9), and terminate into proximal end blocks (166, 176) (as best shown in FIGS. 12A-12C). Intermediary portions (162, 172) may include various segments coupled to each other in order to extend between distal portions (164, 174) and proximal end blocks (166, 176). Various segments of intermediary portions (162, 172) may be coupled through any suitably means as would be apparent to one skilled in the art in view of the teachings herein. Intermediary portions (162, 172) each wrap around a portion of cable driver assembly (210) such that movement of cable driver assembly (210) relative to handle (110) may actuate push-pull cables (160, 170) simultaneously in opposite directions.

As best seen in FIGS. 8-9, cable driver assembly (210) includes central body (212) and a pair of lateral wings (220) extending from central body (212). Cable driver assembly (210) is rotationally coupled with handle (110). Specifically, cable driver (210) is configured to rotate about a drive axis (D-A). Central body (212) includes an annular array of protrusions (214) that together define key slots (215). Key slots (215) are dimensioned to receive torque transfer projections (284) of load limiter assembly (250). As will be described in greater detail below, torque transfer projections (284) are operatively coupled with rocker arm (230) such that suitable rotation of rocker arm (230) relative to handle (110) may drive rotation of cable driver (210) about drive axis (D-A). Central body (212) also defines a hollow interior (216) configured to house selected portions of rocker arm (230) and load limiter assembly (250).

Wings (220) of cable driver assembly (210) are configured to couple with a respective push-pull cable (160, 170) such that rotation of wings (220) about drive axis (D-A) actuates pull cables (160, 170) in accordance with the description herein. Each wing (220) defines a cable recess (222) and a plug opening (224) extending into cable recess (222). Cable recess (222) is dimensioned to receive intermediary portions (162, 172) of push-pull cables (160, 170), while plug opening (224) is dimensioned to receive cable plug (226) such that cable plug (226) actuates with wings (220). Cable recess (220) is dimensioned to accommodate cable plug (226) such that intermediary portions (162, 172) may wrap around cable plug (226) as shown in FIG. 9, thereby suitably coupling intermediary portion (162, 172) of push-pull cables (160, 170) with cable driver assembly (210). Cable plug (226) interacts with respective intermediary portion (162, 172) such that proximal movement of cable plug (226) pulls intermediary portions (162, 172) proximally.

Figure 10A:
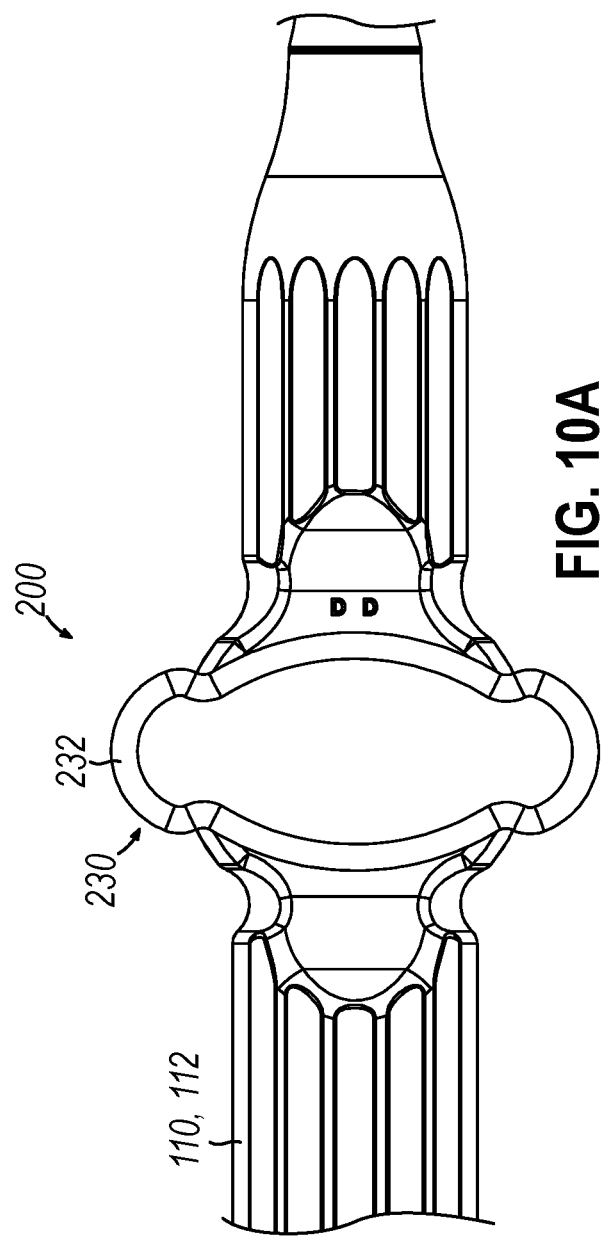
FIG. 10A depicts a top plan view of the handle and the deflection drive assembly of FIG. 6, where an elongated body of the deflection drive assembly is in a first rotational position relative to the handle.

FIGS. 10A-12C show exemplary use of deflection drive assembly (200) to deflect end effector (140) and the distal portion of catheter (120) about central longitudinal axis (L-L). FIGS. 10A, 11A, and 12A show various sections of catheter assembly (100) when end effector (140) is in a neutral, non-deflected position. FIG. 10A shows rocker arm (230) in a neutral rotational position relative to handle (110). As best shown in FIG. 12A, when rocker arm (230) is in the first rotational position, cable driver assembly (210) is in a corresponding first rotation position such that sliding bodies (165, 175), and therefore push-pull cables (160, 170), are in a first longitudinal position associated with end effector (140) being in the non-deflected position as shown in FIG. 11A.

Figure 10B:
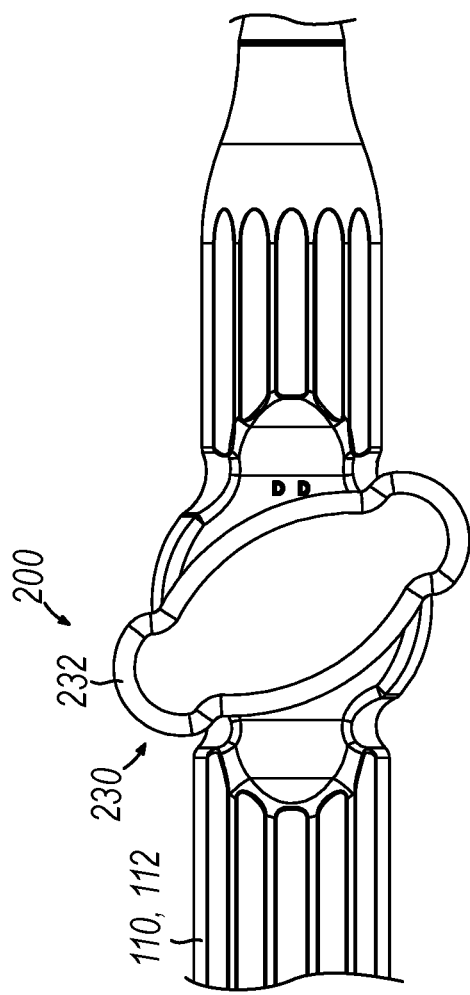
FIG. 10B depicts a top plan view of the handle and the deflection drive assembly of FIG. 6, where the elongated body of FIG. 10A is in a second rotational position relative to the handle.

When the physician (PH) desires to deflect end effector (140) in a first direction relative to central longitudinal axis (L-L) to a first deflected position shown in FIG. 11B, the physician (PH) may rotate rocker arm (230) relative to handle (110) to the position shown in FIG. 10B. As best shown in FIG. 12B, rotation of rocker arm (230) to the rotational position shown in FIG. 10B drives cable driver assembly (210) into a corresponding rotational position such that plug (226) associated with push-pull cable (170) drives push-pull cable (170) proximally. Additionally, plug (226) associated with push-pull cable (160) is driven distally, allowing push-pull cable (160) to actuate distally.

Proximal translation of push-pull cable (170) drives sliding body (175) proximally within the respective sliding channel (106), which also allows sliding body (165) to slide distally within sliding channel (106). Proximal translation of sliding body (175) drives the section of intermediate portion (172) extending distally from sliding body (175), as well as distal portion (174), proximally. Since distal portion (174) may not actuate proximally out of end effector (140), as described above, proximal translation of distal portion (174) drives end effector (140) to bend to the position shown in FIG. 11B.

Figure 10C:
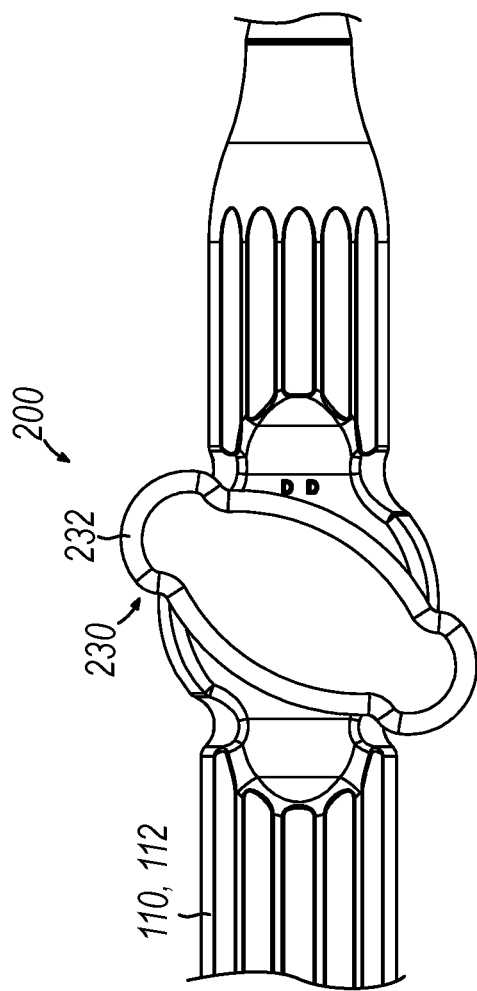
FIG. 10C depicts a top plan view of the handle and the deflection drive assembly of FIG. 6, where the elongated body of FIG. 10A is in a third rotational position relative to the handle.

Similarly, when the physician (PH) desires to deflect end effector (140) in a section direction relative to central longitudinal axis (L-L) to a second deflected position shown in FIG. 11C, the physician (PH) may rotate rocker arm (230) relative to handle (110) to the position shown in FIG. 10C. As best shown in FIG. 12C, rotation of rocker arm (230) to the rotational position shown in FIG. 10C drives cable driver assembly (210) into a corresponding rotational position such that plug (226) associated with push-pull cable (160) drives push-pull cable (160) proximally. Additionally, plug (226) associated with push-pull cable (170) is driven distally, allowing push-pull cable (170) to actuate distally.

Proximal translation of push-pull cable (160) drives sliding body (165) proximally within sliding channel (106), which also allows sliding body (175) slide distally within sliding channel (106). Proximal translation of sliding body (165) drives the section of intermediate portion (162) extending distally from sliding body (165), as well as distal portion (164), proximally. Since distal portion (164) may not actuate proximally out of end effector (140), as described above, proximal translation of distal portion (164) drives end effector (140) to bend to the position shown in FIG. 11C.

Various other suitable mechanisms that may be used to drive push-pull cables (160, 170) in a simultaneous, longitudinally-opposing fashion will be apparent to those skilled in the art in view of the teachings herein.

IV. Exemplary Deflection Load Limiter of Catheter Assembly

As mentioned above, first casing portion (112) includes a pair of stops (115) that may rotationally constrain rocker arm (230) from over rotating relative to handle (110). Preventing rocker arm (230) from over rotating may be desirable, as over rotation may place too much force on push-pull cables (160, 170), which may in turn plastically deform, or otherwise damage, push-pull cables (160, 170).

However, as also mentioned above, push-pull cables (160, 170) may be mechanically grounded relative to handle (110) at different locations relative to handle (110) via tensions blocks (168, 178) and tension adjustment channels (108), which may alter the amount of tension imparted on push-pull cables (160, 170) in response to the angular adjustment of rocker arm (230). Therefore, in some instances, over rotation of rocker arm (230) may occur before rocker arm (230) engages stops (115) such that push-pull cables (160, 170) may be undesirably damaged. It may therefore be desirable to have a feature that is configured to limit the amount of force that rocker arm (230) may impart on cable driver assembly (210), regardless of the rotational position of rocker arm (230) relative to handle (110).

Load limiter assembly (250) is configured to limit the force that rocker arm (230) may impart on cable driver assembly (210). In the current example, load limiter assembly (250) is operatively coupled with rocker arm (230). However, it should be understood that load limiter assembly (250) may be operatively coupled with cable driver assembly (210). Alternatively, selected portions of load limiter assembly (250) may be coupled with rocker arm (230); while other selected portions of load limiter assembly (250) may be operatively coupled with cable driver assembly (210).

Figure 16:
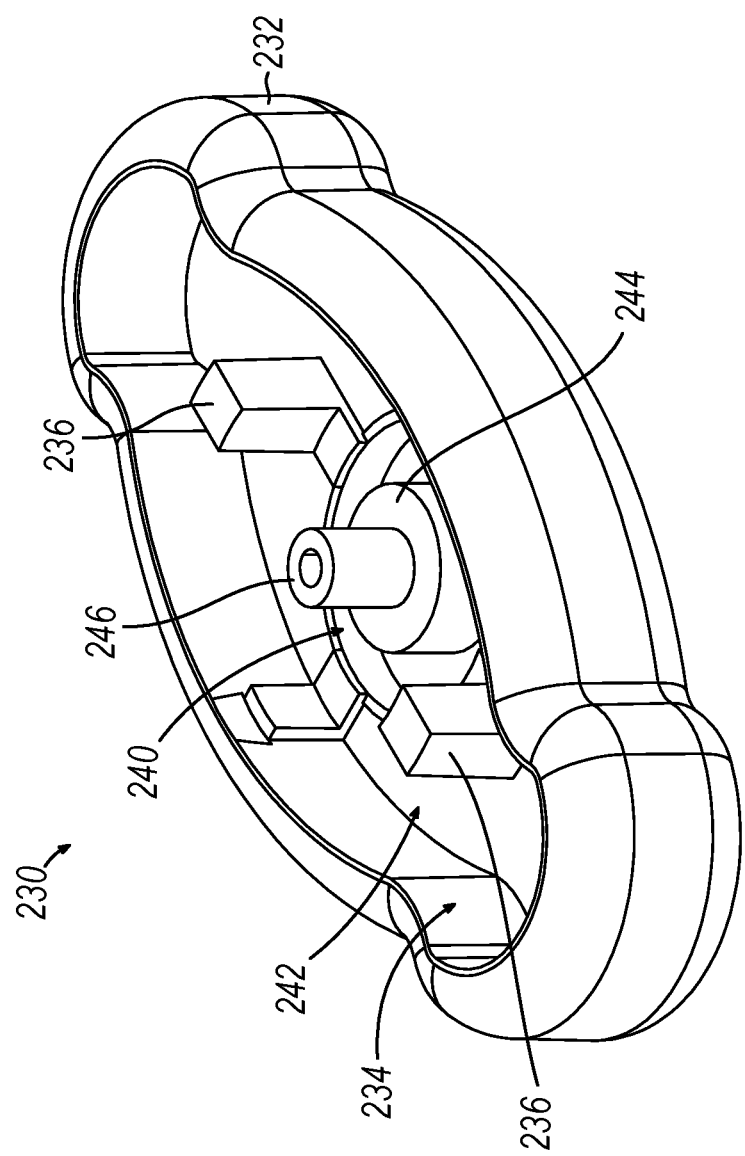
FIG. 16 depicts a perspective view of the elongated body of FIG. 10A.
Figure 17:
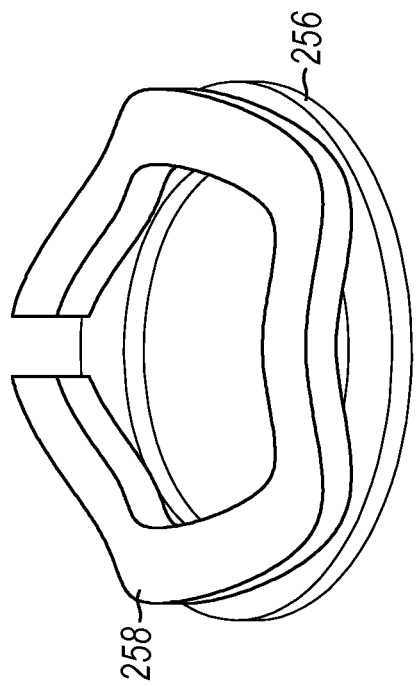
FIG. 17 depicts a perspective view of a contact washer and a wave spring of the load limiter assembly of FIG. 13.

As best shown in FIG. 16, rocker arm (230) includes an elongated body (232) defining a hollow underside (234), two torque transfer projections (236), a first retention collar (244), and threaded channel (246) extending from first retention collar (244). Torque transfer projections (236), first retention collar (244), and threaded channel (246) are located within hollow underside (234) and cooperatively define a housing area (242) dimensioned to house load limiter assembly (250). First retention collar (244) and the underside of elongated body (232) also define an annular recess (240).

Figure 13:
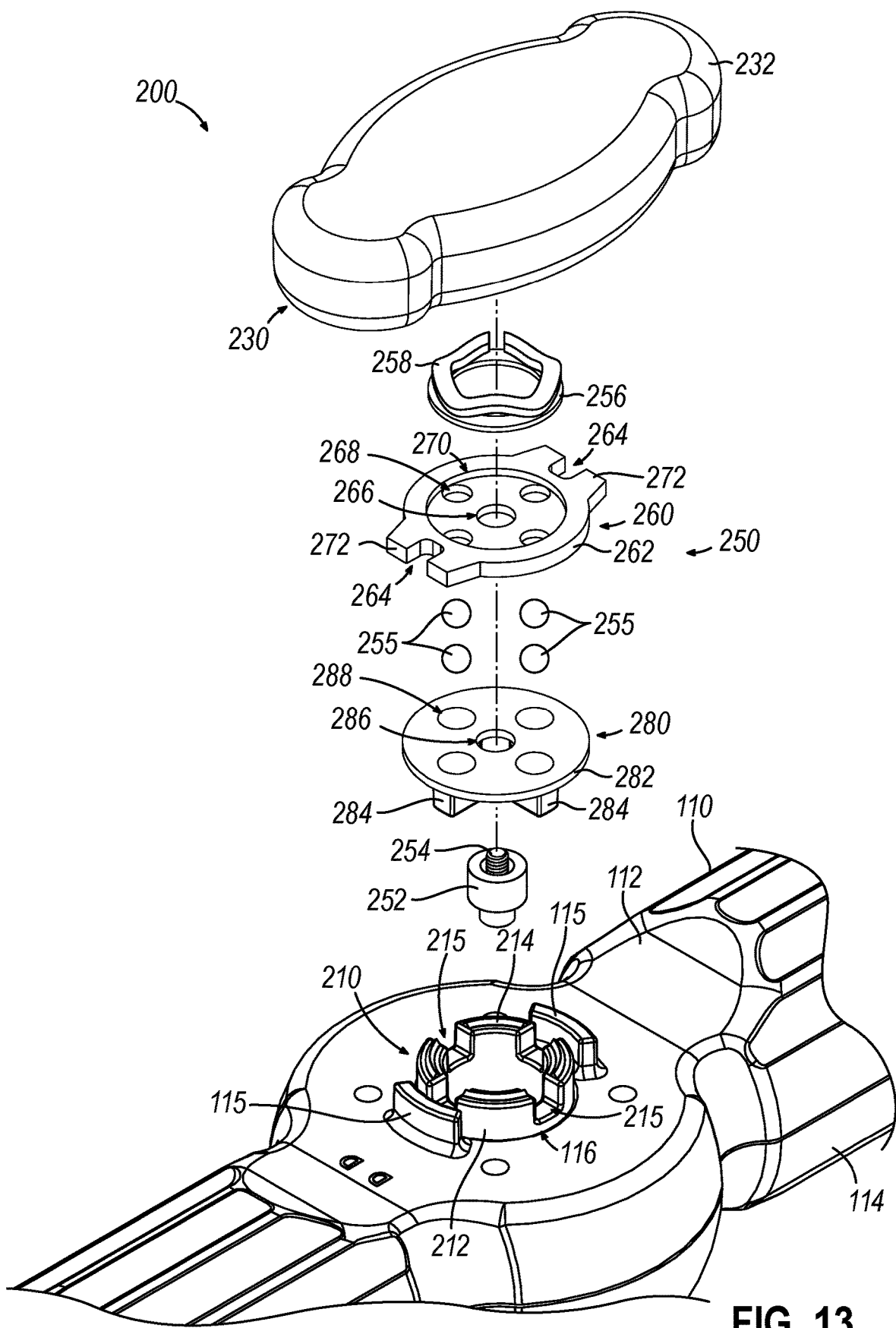
FIG. 13 depicts an exploded perspective view of a load limiter assembly of the deflection drive assembly of FIG. 6.
Figure 15:
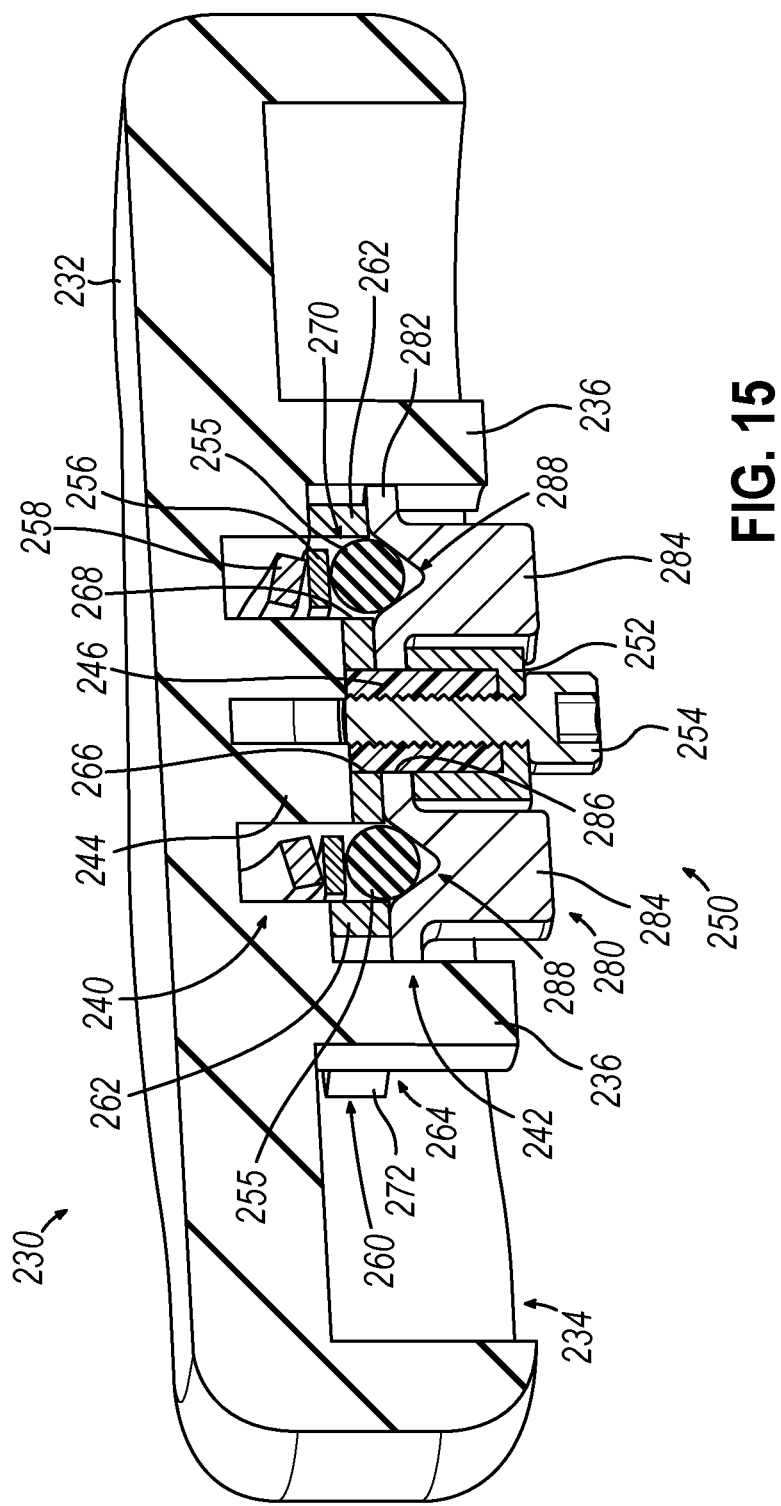
FIG. 15 depicts a cross-sectional perspective view of the elongated body of FIG. 10A and the load limiter assembly of FIG. 13, taken along line 15-15 of FIG. 14.

As best seen in FIGS. 13 and 15, load limiter assembly (250) includes a biasing element (258), a contact washer (256), an arm coupling (260), a plurality of spheres (255), a cable driver coupling (280), a threaded bolt (254), and a second retention collar (252). Plurality of spheres (255) are interposed between arm coupling (260) and cable driver coupling (280). Additionally, plurality of spheres (255) are configured to transition from an engaged configuration and a disengaged configuration when the force imparted from rocker arm (230) to cable driver (210) reaches a predetermined load value that may damage push-pull cables (160, 170).

As will be described in greater detail below, when spheres (255) are in the engaged configuration, spheres (255) may transmit forces between arm coupling (260) and cable driver coupling (280) such that arm coupling (260) and cable driver coupling (280) rotate together, thereby allowing rocker arm (230) to drive cable driver assembly (210) such that push-pull cables (160, 170) may translate to deflect end effector (140). As will also be described in greater detail below, when spheres (255) are in the disengaged configuration, spheres (255) may no longer suitably transmit forces between arm coupling (260) and cable driver coupling (280) such that arm coupling (260) and cable driver coupling (280) do not rotate together, thereby inhibiting rocker arm (230) from driving cable driver assembly (210) such that push-pull cables (160, 170) do not translate.

As best seen in FIG. 15, biasing element (258) and contact washer (256) are dimensioned to be housed within annular recess (240) defined by rocker arm (230) such that contact washer (256) is interposed between biasing element (258) and spheres (255).

As will be described in greater detail below, biasing element (258) is configured to deform in response to a predetermined load value generated from rocker arm (230) attempting to actuate cable driver assembly (210) to thereby deflect end effector (140) in accordance with the description herein. In the current example, biasing element (258) includes a wave spring, but any suitably biasing element (258) may be used as would be apparent to one skilled in the art in view of the teachings herein. For instance, a belleville washer, elastomeric O-ring, coil spring, or any other suitable resilient material or structure may be used as would be apparent to one of skill in the art in view of the teachings herein.

Figure 18:
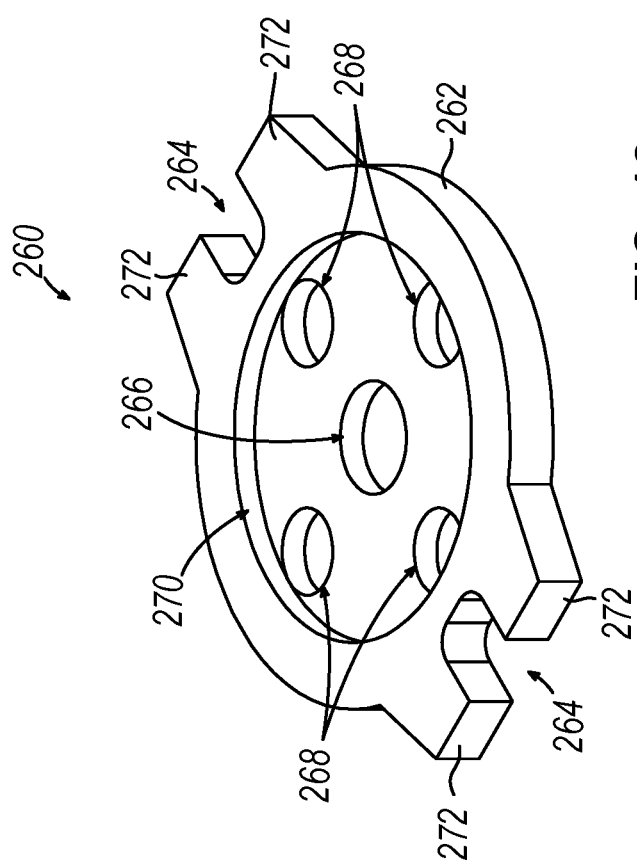
FIG. 18 depicts a perspective view of a handle coupling of the load limiter assembly of FIG. 13.
Figure 19:
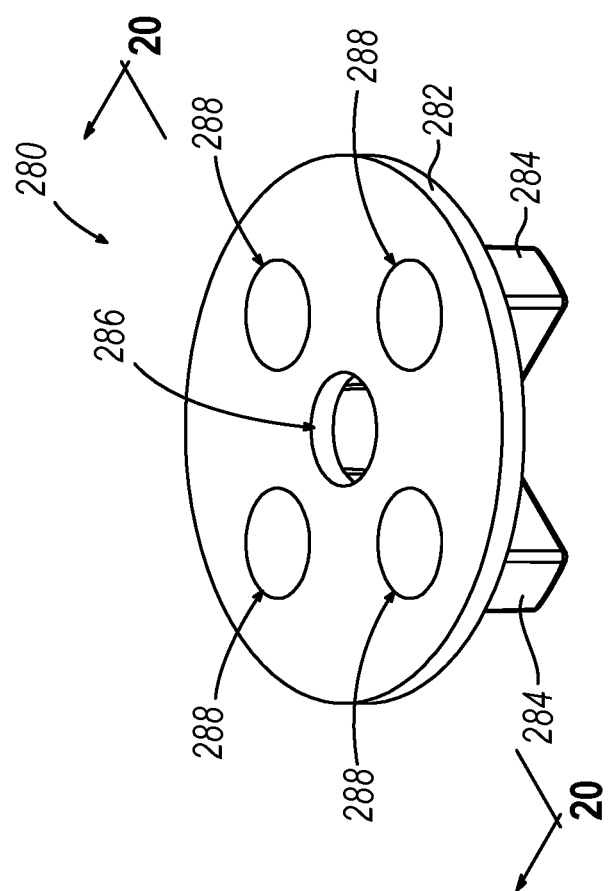
FIG. 19 depicts a perspective view of a cable drive coupling of the load limiter assembly of FIG. 13.

As best shown in FIG. 18, arm coupling (260) includes a body (262) having lateral nubs (272) defining a pair of lateral notches (264). Body (262) further defines a central through hole (266), a plurality of sphere housing through holes (268), and a central recess (270).

As best seen in FIG. 15, central through hole (266) is dimensioned to slide over an exterior of threaded channel (246) until a face of body (262) contacts first retention collar (244). Therefore, central through hole (266) is configured to couple arm coupling (260) with arm rocker (230).

Figure 14:
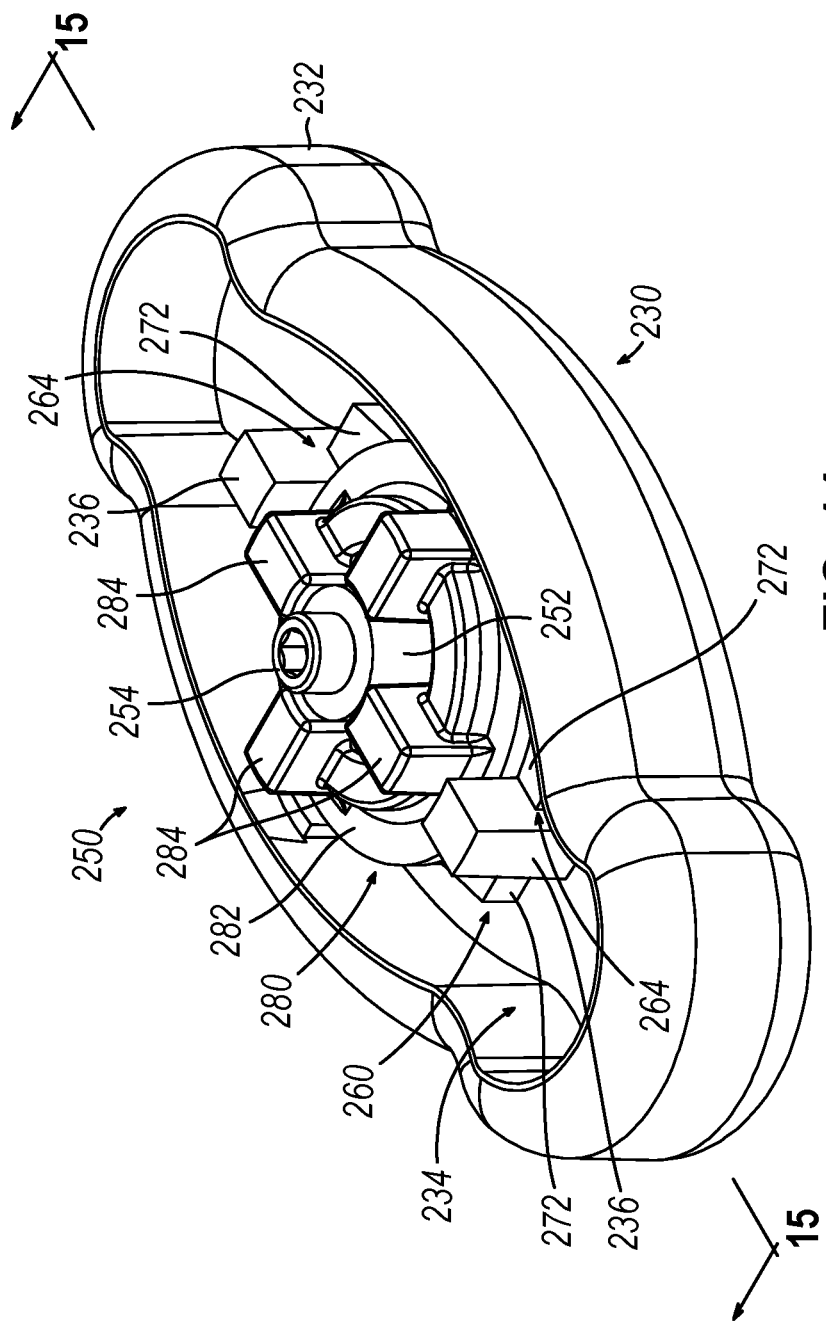
FIG. 14 depicts a perspective view of the elongated body of FIG. 10A and the load limiter assembly of FIG. 13.

As best seen in FIG. 14, lateral notches (264) are dimensioned to receive torque transfer projections (236) of rocker arm (230). Therefore, contact between torque transfer projections (236) and lateral nubs (272) ensures rotation of rocker arm (230) causes rotation of arm coupling (260).

Sphere housing through holes (268) are dimensioned to slidably house a respective sphere (255). In particular, sphere housing through holes (268) are dimensioned to contain a respective sphere (255) such that sphere (255) rotates with rocker arm (230) and arm coupling (260) about drive axis (D-A), but also such that sphere (255) may translate within through hole (268) between an engaged configuration and a disengaged configuration. In the current example, spheres (255) may translated relative to arm coupling (260) along an axis that is parallel to drive axis (D-A), however this is merely optional, as spheres (255) may translate along any suitable axis as would be apparent to one of skill in the art in view of the teachings herein.

Cable driver coupling (280) includes a body (282) and a plurality of torque transfer projections (284). Body (282) of cable driver coupling (280) also defines central through hole (286) and a plurality of sphere housing pockets (288). Similar to central through hole (266) of arm coupling (260), central through hole (286) is dimensioned to slide over an exterior of threaded channel (246) such that central through hole (286) is configured to couple cable driver coupling (280) with arm rocker (230).

As best seen in FIG. 15, with central through holes (266, 286) of arm coupling (260) and cable driver coupling (280), respectively, inserted over the exterior of threaded channel (246), threaded bolt (254) and second retention collar (252) may be attached threaded channel (246) of rocker arm (230). Threaded bolt (254) and threaded channel (246) include complementary threading that mesh with each other. Second retention collar (252) may slide over an exterior portion of threaded channel (246) in order to suitably contact body (282) of cable driver coupling (280) once threaded bolt (254) is suitably coupled with threaded channel (246). Therefore, second retention collar (252), first retention collar (244), threaded bolt (254), and threaded channel (246) keep bodies (262, 282) of arm coupling (260) and cable driver coupling (280) suitably coupled.

Second retention collar (252) includes a suitable length such that when threaded bolt (252) is suitably coupled with threaded channel (246), as shown in FIG. 15, the frictional braking force imparted by contact between bodies (262, 282) is not strong enough such that bodies (262, 282) do not require spheres (254) (or any other suitably force transfer member) to be in the engaged configuration in order for bodies (262, 282) to rotate together about drive axis (D-A). In other words, threaded bolt (254) and retention collars (244, 252) do not overly compress bodies (262, 282) together such that bodies (262, 282) may not rotate together when spheres (254) transition into the disengaged configuration in accordance with the description herein.

As mentioned above, torque transfer projections (284) are configured to fit within key slot (215) of cable driver assembly (210) such that torque transfer projections (284) abut against annular protrusions (214) of central body (212). Therefore, torque transfer projections (284) are attached to cable driver coupling (280) such that rotation of cable driver coupling (280) about drive axis (D-A) leads to rotation of cable driver assembly (210) about drive axis (D-A). Therefore, while arm coupling (260) is rotationally fixed to rocker arm (230), cable driver coupling (280) is rotationally fixed to cable driver assembly (210).

Sphere housing pockets (288) are dimensioned to selectively house a respective sphere (255) in conjunction with sphere housing through hole (268) of arm coupling (260). As best seen in FIG. 15, biasing element (258) biases contact washer (256) into sufficient engagement with spheres (255) such that spheres (255) are biased against the angled surfaces of sphere housing pockets (288). Sphere housing pockets (288) include angled surfaces that are oriented to provide a camming force on spheres (255) that is at least partially aligned with the direction spheres (255) travel between the engaged configuration and the disengaged configuration. In particular, the camming force on spheres (255) is generated as a reactionary force when spheres (255) attempt to transfer forces from arm coupling (260) to cable driver coupling (280).

Figure 21A:
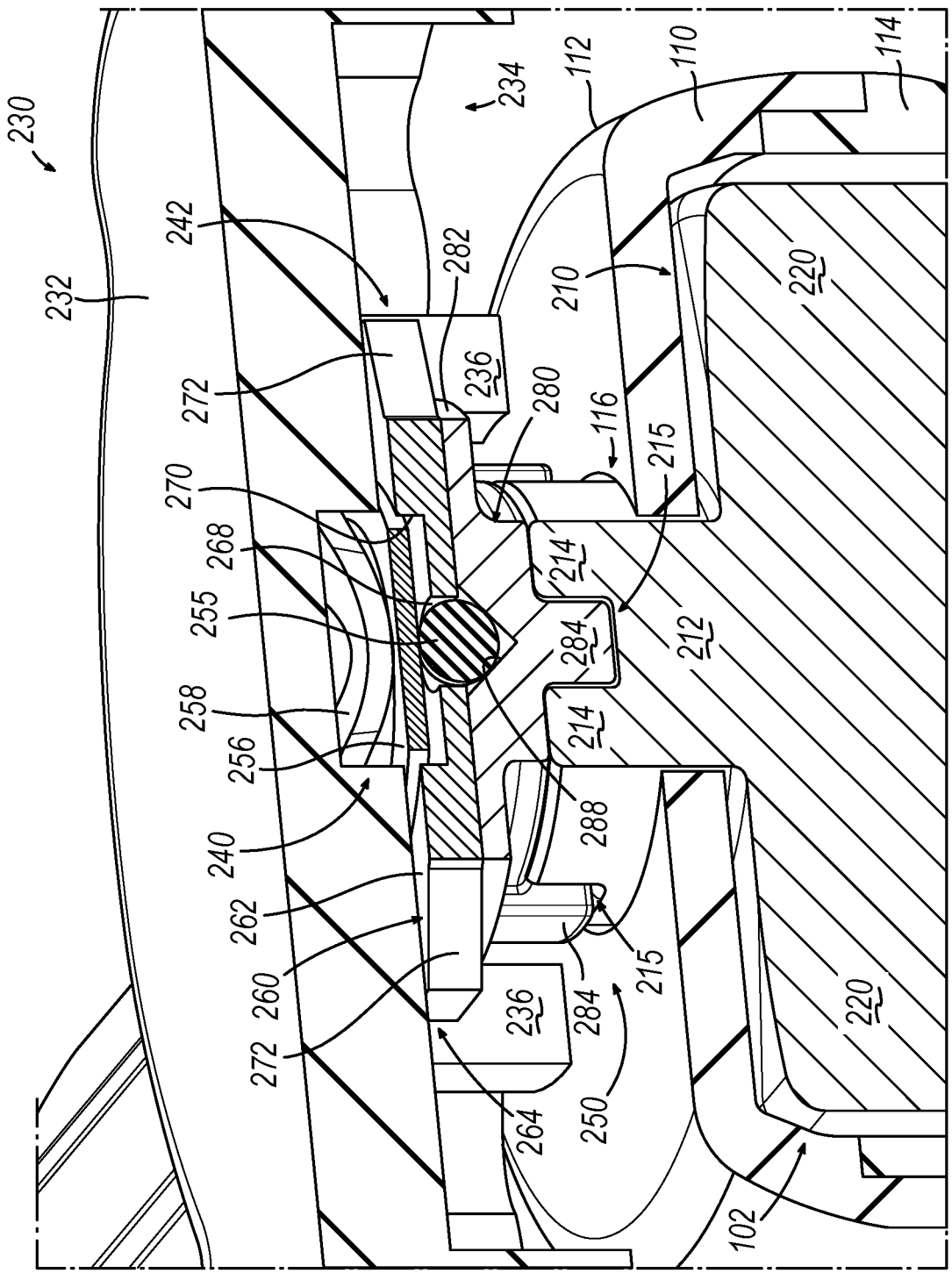
FIG. 21A depicts a cross-sectional perspective view, taken along line 21-21 of FIG. 6, where the load limiter assembly of FIG. 13 is in an engaged position.
Figure 21B:
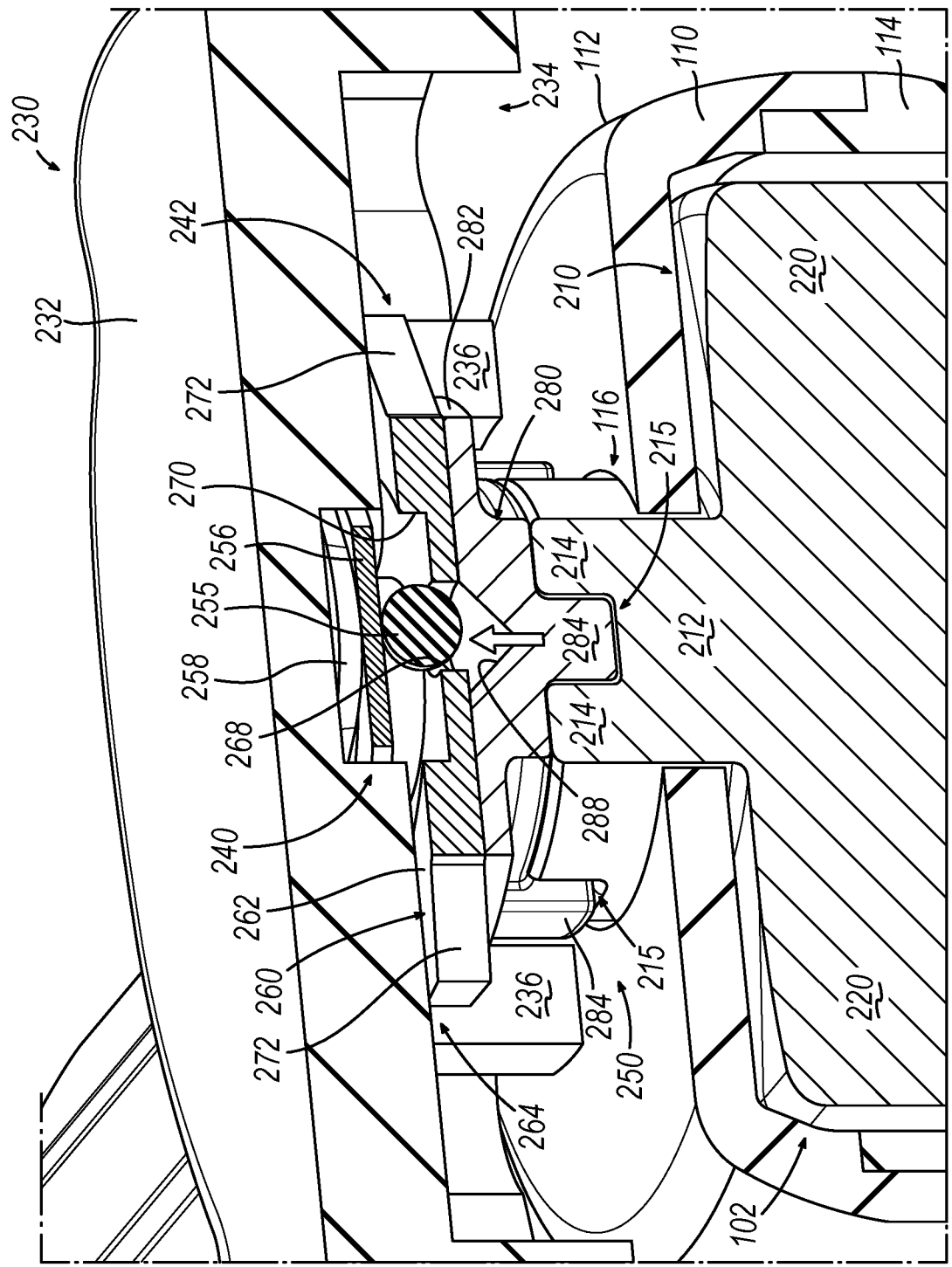
FIG. 21B depicts a cross-sectional perspective view, taken along line 21-21 of FIG. 6, where the load limiter assembly of FIG. 13 is in an initial disengaged position such that the elongated body of FIG. 10A and the hand coupling of FIG. 18 are not rotated relative to the cable drive coupling of FIG. 19.
Figure 21C:
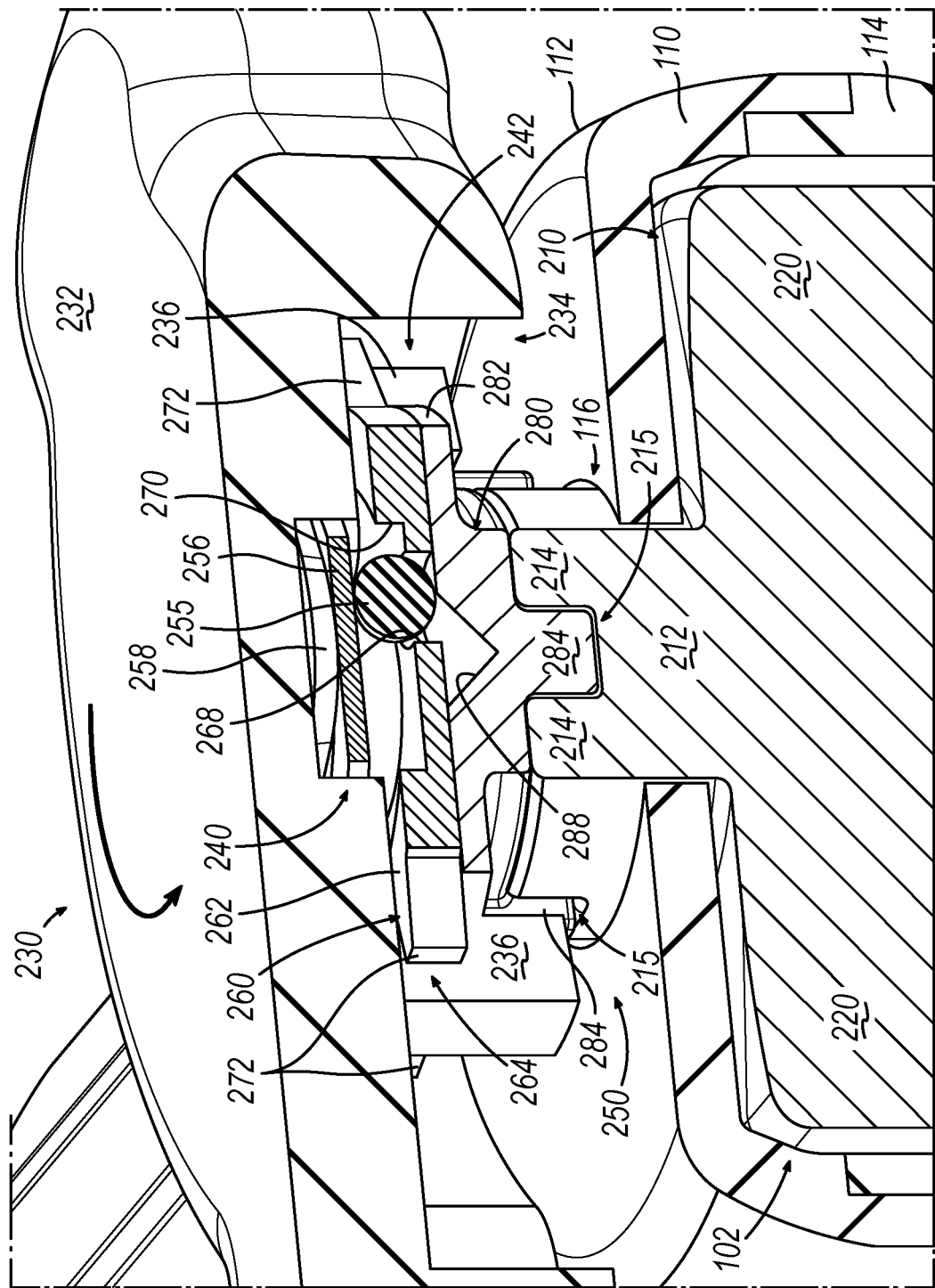
FIG. 21C depicts a cross-sectional perspective view, taken along line 21-21 of FIG. 6, where the load limiter assembly of FIG. 13 is in a subsequent disengaged position such that the elongated body of FIG. 10A and the hand coupling of FIG. 18 are rotated relative to the cable drive coupling of FIG. 19.

FIGS. 21A-21C show an exemplary use of load limiter assembly (250) while rocker arm (230) actuates cable driver assembly (210) in order to translate push-pull cables (160, 170) in accordance with the description herein. FIG. 21A shows spheres (255) of load limiter assembly (250) in the engaged position. Therefore, biasing member (258) biases spheres (255) against sphere housing pockets (288) such that spheres (255) may transfer loads from arm coupling (260) to cable driver coupling (280).

In particular, the physician (PH) may rotate rocker arm (230) in accordance with the description herein, causing torque transfer projections (236) to transfer force to lateral nubs (272) of arm coupling (260), thereby rotating body (262) of arm coupling (260). The portion of body (262) defining sphere housing through holes (268) of arm coupling (260) may then abut against spheres (255) to transfer the force provided by torque transfer projections (236) to spheres (255). Spheres (255) may then transfer this force to body (282) of cable driver coupling (280) by abutting against angled surfaces defining sphere housing pockets (288), which in turn rotates cable driver coupling (280) and cable driver assembly (210) to translate push-pull cables (160, 170) in accordance with the description herein.

It should be understood at the moment shown in FIG. 21A, the reactionary upward camming force imparted on spheres (255) by angled surfaces defining sphere housing pockets (288) is smaller than the downward biasing force imparted on spheres (255) by biasing member (258). Therefore, spheres (255) remain engaged with angled surfaces defining sphere housing pockets (288), allowing rocker arm (230) to deflect end effector (140) in accordance with the description herein.

FIG. 21B shows the moment when rocker arm (230) imparts a force on cable driver assembly (210) at a pre-determined load threshold. The pre-determined load threshold may be determined based off any desirable characteristic as would be apparent to one of skill in the art in view of the teachings herein. For instance, the pre-determined load threshold may be a force value corresponding to driving cable driver assembly (210) such that push-pull cables (160, 170) experience failure, plastic deformation, etc.

When the physician (PH) rotates rocker arm (230) to the pre-determined load threshold, the reactionary camming force which sphere housing pockets (288) imparts on spheres (255) is sufficient to overcome the downward biasing force biasing element (258) imparts on spheres (255). Therefore, spheres (255) are pushed upward in the disengaged configuration such that spheres (255) are no longer suitably engaged with the angled surfaces forming sphere housing pockets (288). It should be understood that biasing member (258) is compressed in order to allow spheres (255) to transition into the disengaged configuration.

With spheres (255) actuated into the disengaged configuration, spheres (255) may not transfer forces from arm coupling (260) to cable driver coupling (280). Therefore, as shown in FIG. 21C, if the physician (PH) attempts to further rotate rocker arm (230) after spheres (255) transition to the disengaged configuration, rocker arm (230), arm coupling (260), and spheres (255) rotate without rotating cable driver assembly (210). Therefore, further rotation of rocker arm (230) to the position shown in FIG. 21C causes arm coupling (260) to slip relative to cable driver coupling (280) such that rocker arm (230) is prevented from further driving cable driver assembly (210) to translate push-pull cables (160, 170). This may help prevent the physician (PH) from inadvertently damaging push-pull cables (160, 170).

At the moment shown in FIG. 21C, the physician (PH) may rotate rocker arm (230) back to the position of FIG. 21A so spheres (255) reenter the engaged configuration, thereby allowing the physician (PH) to regain suitably control of deflecting end effector (140).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a handle; (b) a catheter extending distally from the handle, a proximal portion of the catheter defining a longitudinal axis; (c) an end effector extending distally from the catheter, the end effector including at least one electrode; (d) a deflection assembly, the deflection assembly being configured to deflect the end effector away from the longitudinal axis, the deflection assembly comprising: (i) an input member associated with the handle, and (ii) a translating assembly coupled to the end effector, the input member being configured to drive the translating assembly to deflect the end effector away from the longitudinal axis; (e) a load limiting assembly, where the load limiting assembly is configured to decouple the input member from the translating assembly at a predetermined load such that the input member is inhibited from driving the translating assembly when the input member is decoupled by the load limiting assembly.

Example 2

The apparatus of Example 1, the deflection assembly further comprising a rotating driver interposed between the input member and the translating assembly.

Example 3

The apparatus of Example 2, the translating assembly comprising a pair of push-pull cables, the rotating drive being configured to drive the pair of push-pull cables in opposing directions simultaneously.

Example 4

The apparatus of any one or more of Examples 2 through 3, the load limiting assembly being interposed between the rotating driver and the input member.

Example 5

The apparatus of any one or more of Examples 1 through 4, the load liming assembly comprising at least one engagement member configured to transition between an engaged configuration and a disengaged configuration, the load limiting assembly being configured to decouple the input member from the translating assembly in the disengaged configuration.

Example 6

The apparatus of Example 5, the load limiting assembly comprising a biasing member configured to bias the at least one engagement member into the engaged configuration.

Example 7

The apparatus of any one or more of Examples 5 through 6, the at least one engagement member comprising at least one sphere.

Example 8

The apparatus of Example 7, the at least one sphere comprising four spheres.

Example 9

The apparatus of any one or more of Examples 6 through 8, the biasing member comprising a wave spring.

Example 10

The apparatus of any one or more of Examples 6 through 8, the biasing member comprising an elastomeric o-ring.

Example 11

The apparatus of any one or more of Examples 6 through 8, the biasing member comprising a compression spring.

Example 12

The apparatus of any one or more of Examples 1 through 11, the input member comprising a knob configured to rotate relative to the handle about a drive axis.

Example 13

The apparatus of Example 12, the drive axis being perpendicular with the longitudinal axis.

Example 14

The apparatus of any one or more of Examples 1 through 13, the at least one electrode being configured to emit RF energy.

Example 15

The apparatus of any one or more of Examples 1 through 14, the at least one electrode being configured to perform electrophysiology mapping.

Example 16

The apparatus of any one or more of Examples 1 through 15, the end effector comprising a strain gauge assembly.

Example 17

The apparatus of any one or more of Examples 1 through 16, the end effector being configured to emit irrigation fluid.

Example 18

The apparatus of any one or more of Examples 1 through 17, the end effector comprising a position sensor.

Example 19

The apparatus of any one or more of Examples 1 through 18, the load limiting assembly comprising a first body associated with the input member and a second body associated with the translating assembly, the first body and the second body being configured to slip relative to each other when the load limiting assembly is decoupling the input member from the translating assembly.

Example 20

The apparatus of Example 19, the first body and the second body being coupled with each other via a retention collar.

Example 21

The apparatus of any one or more of Examples 19 through 20, the first body and the second body being coupled via a threaded bolt.

Example 22

An apparatus, comprising: (b) a flexible catheter assembly comprising a proximal portion and a distal portion, the proximal portion defining a longitudinal axis; (c) an end effector extending attached to the distal portion of the flexible catheter assembly, the end effector including at least one electrode; (d) a deflection assembly, the deflection assembly being configured to deflect the end effector away from the longitudinal axis; and (e) a load limiting assembly, the load limiting assembly being configured to decouple the deflection assembly at a predetermined load such that the input member is inhibited from driving the translating assembly when the deflection assembly is decoupled by the load limiting assembly.

Example 23

An apparatus comprising: (a) a handle; (b) a flexible catheter extending distally from the handle, a proximal portion of the flexible catheter defining a longitudinal axis; (c) an end effector extending distally from the catheter, the end effector including at least one electrode; (d) a deflection assembly, the deflection assembly being configured to deflect the end effector away from the longitudinal axis, the deflection assembly comprising: (i) an input member associated with the handle, and (ii) a translating assembly coupled to the end effector, the input member being configured to drive the translating assembly to deflect the end effector away from the longitudinal axis; and (e) a load limiting assembly comprising a biasing member interposed between the input member and the translating assembly, the load limiting assembly being configured to transition between an engaged configuration and a disengaged configuration, the load limiting assembly being configured to decouple the input member from the translating assembly at a predetermined load such that the input member is inhibited from driving the translating assembly in the disengaged configuration, the load limiting assembly being configured to permit the input member to drive the translating assembly in the engaged configuration, the biasing member biasing the load limiting assembly toward the engaged configuration.

VI. Miscellaneous

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

By way of example only, when one of the instruments described herein is cleaned and sterilized before and/or after a procedure such cleaning and reprocessing may be carried out using a solution. By way of further example only, such a solution may comprise a chemical selected from a group consisting of: 3300-3800 ppm peracetic acid; 2.65% glutaraldehyde; 3.4% glutaraldehyde with 26% isopropanol; 3.5% glutaraldehyde; 5.75% ortho-phthaldehyde; 0.55% ortho-phthaldehyde; hypochlorite with hypochlorous acid 650-675 ppm active free chlorine; 1.12% glutaraldehyde with 1.93% phenol/phenate; 2.5% glutaraldehyde; 3.2% glutaraldehyde; 3% glutaraldehyde; 7.35% hydrogen peroxide with 0.23% peracetic acid; 1.0% hydrogen peroxide with 0.08% peracetic acid; 2.4% glutaraldehyde; 3.4% glutaraldehyde; 2.0% hydrogen peroxide; 0.60% ortho-phthalaldehyde; hypochlorous acid/hypochlorite 400-450 ppm with active free chlorine; and combinations thereof. As another merely illustrative example, such a solution may comprise a chemical selected from a group consisting of: 3100-3400 ppm peracetic acid; 3.4% glutaraldehyde with 20.1% isopropanol; 2.0% hydrogen peroxide; at least 1820 mg/L peracetic acid; 0.575% ortho-phthalaldehyde; 0.60% ortho-phthalaldehyde; hypochlorite and hypochlorous acid with 650-675 ppm active free chlorine; 0.55% ortho-phthalaldehyde; 7.5% hydrogen peroxide; 2.6% glutaraldehyde; hypochlorite and hypochlorous acid with 400-450 ppm active free chlorine; 0.55% ortho-phthalaldehyde; and combinations thereof.

By way of example only, when one of the instruments described herein is cleaned and sterilized before and/or after a procedure such cleaning and reprocessing may be carried out using a sterilization system such as those described in U.S. Pat. No. 6,939,519, entitled "Power System for Sterilization Systems Employing Low Frequency Plasma," issued Sep. 6, 2005, the disclosure of which is incorporated by reference herein in its entirety; U.S. Pat. No. 6,852,279, entitled "Sterilization with Temperature-Controlled Diffusion Path," issued Feb. 8, 2005, the disclosure of which is incorporated by reference herein, in its entirety; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein, in its entirety; U.S. Pat. No. 6,447,719, entitled "Power System for Sterilization Systems Employing Low Frequency Plasma," issued Sep. 10, 2002, the disclosure of which is incorporated by reference herein, in its entirety; and U.S. Pub. No. 2017/0252474, entitled "Method of Sterilizing Medical Devices, Analyzing Biological Indicators, and Linking Medical Device Sterilization Equipment" published Sep. 7, 2017, the disclosure of which is incorporated by reference herein, in its entirety. Some sterilization systems may use vaporized chemical sterilants or chemical gas such as hydrogen peroxide, peracetic acid, ozone, chlorine dioxide, nitrogen dioxide, etc., to sterilize medical devices. Examples of such systems are described in U.S. Pat. No. 6,365,102, entitled "Method of Enhanced Sterilization with Improved Material Compatibility," issued Apr. 2, 2002, the disclosure of which is incorporated by reference herein, in its entirety; and U.S. Pat. No. 6,325,972, entitled "Apparatus and Process for Concentrating a Liquid Sterilant and Sterilizing Articles Therewith," issued Dec. 4, 2001, the disclosure of which is incorporated by reference herein, in its entirety.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a handle;
   (b) a catheter extending distally from the handle, a proximal portion of the catheter defining a longitudinal axis;
   (c) an end effector extending distally from the catheter, the end effector including at least one electrode;
   (d) a deflection assembly, the deflection assembly being configured to deflect the end effector away from the longitudinal axis, the deflection assembly comprising:
      (i) an input member associated with the handle, the input member comprising a driving body configured to actuate relative to the handle,
      (ii) a translating assembly coupled to the end effector, the driving body being configured to actuate relative to the handle to thereby drive the translating assembly to deflect the end effector away from the longitudinal axis;
   (e) a load limiting assembly comprising a resilient member interposed between the input member and the translating assembly, the load limiting assembly configured to cause the deflection assembly to move between an engaged configuration and a disengaged configuration, where in the engaged configuration the input member is coupled to the translating assembly such that actuation of the input member drives the translating assembly to deflect the end effector away from the longitudinal axis, and in the disengaged configuration the input member is decoupled from the translating assembly such that actuation of the input member moves the input member without driving the translating assembly, the load limiting assembly being configured to cause the deflection assembly to move to the disengaged configuration when actuation of the input member results in generation of a predetermined load against the resilient member.

2. The apparatus of claim 1, the at least one electrode being configured to emit RF energy.

3. The apparatus of claim 1, the at least one electrode being configured to perform electrophysiology mapping.

4. The apparatus of claim 1, the end effector being configured to emit irrigation fluid.

5. The apparatus of claim 1, the end effector comprising a position sensor.

6. The apparatus of claim 1, the input member comprising a knob configured to rotate relative to the handle about a drive axis.

7. The apparatus of claim 6, the drive axis being perpendicular with the longitudinal axis.

8. The apparatus of claim 1, the load limiting assembly comprising a first body associated with the input member and a second body associated with the translating assembly, the first body and the second body being configured to slip relative to each other in the disengaged configuration.

9. The apparatus of claim 8, the first body and the second body being coupled with each other via a retention collar.

10. The apparatus of claim 1, the deflection assembly further comprising a rotating driver interposed between the input member and the translating assembly.

11. The apparatus of claim 10, the translating assembly comprising a pair of push-pull cables, the rotating driver being configured to drive the pair of push-pull cables in opposing directions simultaneously.

12. The apparatus of claim 10, the load limiting assembly being interposed between the rotating driver and the input member.

13. The apparatus of claim 1, the load limiting assembly comprising at least one engagement member configured to transition between the engaged configuration and the disengaged configuration.

14. The apparatus of claim 13, the at least one engagement member comprising at least one sphere.

15. The apparatus of claim 13, the resilient member being configured to bias the at least one engagement member into the engaged configuration.

16. The apparatus of claim 15, the resilient member comprising a wave spring.

17. The apparatus of claim 15, the resilient member comprising an elastomeric o-ring.

18. The apparatus of claim 15, the resilient member comprising a compression spring.

19. An apparatus, comprising:
(a) a flexible catheter assembly comprising a proximal portion and a distal portion, the proximal portion defining a longitudinal axis;
(b) an end effector attached to the distal portion of the flexible catheter assembly, the end effector including at least one electrode;
(c) a deflection assembly comprising a pull wire, the deflection assembly being configured to deflect the end effector away from the longitudinal axis;
(d) a rotatable knob configured to drive the deflection assembly; and
(d) a load limiting assembly comprising a resilient member, the load limiting assembly being configured to cause the deflection assembly to move between an engaged configuration and a disengaged configuration, where in the engaged configuration the rotatable knob is coupled to the deflection assembly such that rotation of the rotatable knob drives the deflection assembly to deflect the end effector away from the longitudinal axis, and in the disengaged configuration the deflection assembly is decoupled from the rotatable knob such that rotation of the rotatable knob rotates the rotatable knob without driving the deflection assembly, the load limiting assembly being configured to cause the deflection assembly to move to the disengaged configuration when rotation of the rotatable knob results in generation of a predetermined load against the resilient member.

20. An apparatus comprising:
(a) a handle;
(b) a flexible catheter extending distally from the handle, a proximal portion of the flexible catheter defining a longitudinal axis;
(c) an end effector extending distally from the catheter, the end effector including at least one electrode;
(d) a deflection assembly, the deflection assembly being configured to deflect the end effector away from the longitudinal axis, the deflection assembly comprising:
  (i) an input member associated with the handle, and
  (ii) a translating assembly coupled to the end effector, the input member being configured to drive the translating assembly to deflect the end effector away from the longitudinal axis; and
(e) a load limiting assembly comprising a biasing member comprising a spring interposed between the input member and the translating assembly, the load limiting assembly being configured to cause the deflection assembly to transition between an engaged configuration and a disengaged configuration, where in the disengaged configuration the input member is decoupled from the translating assembly such that the actuation of the input member moves the input member without driving the translating assembly, and in the engaged configuration actuation of the input member drives the translating assembly, the load limiting assembly being configured to cause the deflection assembly to move to the disengaged configuration when actuation of the input member results in generation of a predetermined load against the biasing member, and the biasing member biasing the load limiting assembly toward the engaged configuration.

* * * * *

UNITED STATES PATENT AND TRADEMARK OFFICE
CERTIFICATE OF CORRECTION

| | |
|---|---|
| PATENT NO. | : 11,744,480 B2 |
| APPLICATION NO. | : 15/930795 |
| DATED | : September 5, 2023 |
| INVENTOR(S) | : Ryan Hoitink et al. |

It is certified that error appears in the above-identified patent and that said Letters Patent is hereby corrected as shown below:

In the Claims

In Column 23, Line 28, in Claim 19, delete "(d)" and insert -- (e) --.

Signed and Sealed this
Twenty-eighth Day of November, 2023

Katherine Kelly Vidal
*Director of the United States Patent and Trademark Office*